(12) United States Patent
Greene et al.

(10) Patent No.: US 9,206,258 B2
(45) Date of Patent: Dec. 8, 2015

(54) ANTI-PROSTATE CANCER ANTIBODIES AND METHODS OF DETECTION AND TREATMENT OF PROSTATE CANCER USING THE SAME

(71) Applicant: The Trustees of the University of Pennsylvania, Philadelphia, PA (US)

(72) Inventors: Mark I. Greene, Penn Valley, PA (US); Hongtao Zhang, Paoli, PA (US); Geng Zhang, Bethesda, MD (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 2 days.

(21) Appl. No.: 14/295,495

(22) Filed: Jun. 4, 2014

(65) Prior Publication Data
US 2014/0348831 A1 Nov. 27, 2014

Related U.S. Application Data

(63) Continuation of application No. 13/516,305, filed as application No. PCT/US2010/060782 on Dec. 16, 2010, now abandoned.

(60) Provisional application No. 61/287,063, filed on Dec. 16, 2009.

(51) Int. Cl.
*C07K 16/30* (2006.01)
*G01N 33/574* (2006.01)

(52) U.S. Cl.
CPC ...... *C07K 16/3069* (2013.01); *G01N 33/57407* (2013.01); *G01N 33/57434* (2013.01)

(58) Field of Classification Search
None
See application file for complete search history.

(56) References Cited

U.S. PATENT DOCUMENTS

| | | | |
|---|---|---|---|
| 5,314,996 A | 5/1994 | Wright | |
| 5,763,202 A | 6/1998 | Horoszewicz | |
| 6,319,690 B1 | 11/2001 | Little et al. | |
| 6,541,212 B2 | 4/2003 | Reiter et al. | |
| 6,677,157 B1 | 1/2004 | Cohen | |
| 2004/0105865 A1 | 6/2004 | Bander | |
| 2009/0181015 A1 | 7/2009 | Presta et al. | |

FOREIGN PATENT DOCUMENTS

| | | | |
|---|---|---|---|
| WO | WO 2005/094882 | * 10/2005 | ........... A61K 39/395 |
| WO | WO 2011/084605 A1 | 7/2011 | |

OTHER PUBLICATIONS

Abe A, et al., "Improved inhibitors of glucosylceramide synthase", J Biochem. Feb. 1992;111(2):191-6.
Akiyama Y, et al., "Induction of mouse IgG2a- and IgG3-dependent cellular cytotoxicity in human monocytic cells (U937) by immune interferon", Cancer Res. Nov. 1984;44(11):5127-31.
Brown DA, et al, "Functions of lipid rafts in biological membranes", Annu Rev Cell Dev Biol. 1998;14:111-36.
Carroll, AM, et al., "Monoclonal antibodies to tissue-associated antigens as antitumor reagents", Sury Synth Pathol Res. 1984;3(3):189-200.
Carroll, AM, et al., "Monoclonal antibodies to tissue-specific cell surface antigens. I. Characterization of an antibody to a prostate tissue antigen", Clin Immunol Immunopathol. Nov. 1984;33(2):268-81.
Chai, W., M. S. Stoll, et al., "Neoglycolipid technology: deciphering information content of glycome", Methods Enzymol. 2003;362:160-95.
Correa, J.J. (2006) "Internalization of Antibodies" In Tumor Targeting in Cancer Therapy, M. Page, (Ed.), Humana Press Inc., Totowa, NJ, 2006, pp. 391-409.
Dal Pra, A. et al. "Combining radiation therapy and androgen deprivation for localized prostate cancer—a critical review", Curr Oncol. Oct. 2010;17(5):28-38.
Feizi, T., M. S. Stoll, et al. "Oligosaccharide microarrays to decipher the glyco code", Nat Rev Mol Cell Biol. Jul. 2004;5(7):582-8.
Foley R, et al., "Androgen-hypersensitive preclinical model of prostate cancer" by Kawata et al. Prostate. May 2011;71(6):559-60. Epub Oct. 13, 2010.
Foley, R. et al., "Androgen hypersensitivity in prostate cancer: molecular perspectives on androgen deprivation therapy strategies", Prostate. Apr. 2011;71(5):550-7. Epub Oct. 13, 2010.
Hakomori S, "Structure, organization, and function of glycosphingolipids in membrane", Curr Opin Hematol. Jan. 2003;10(1):16-24.
Liu, Y., A. S. Palma, et al. "Carbohydrate microarrays: key developments in glycobiology", Biol Chem. Jul. 2009;390(7):647-56.
Llorente et al., "Caveolin-1 and MAL are located on prostasomes secreted by the prostate cancer PC-3 cell line", J. Cell Sci.,Oct. 2004, 117(Pt. 22):5343-5351.
Paul P, et al., "Simultaneous determination of sugar incorporation into glycosphingolipids and glycoproteins", Anal Biochem. Aug. 1, 1992 ;204(2):265-72.
Poul, M. et al., "Selection of Tumor-Specific Internalizing Human Antibodies from Phage Libraries", J. Mol. Biol., 2000, 301, 1149-1161.
Sumey, C. et al., "Adjuvant medical therapy for prostate cancer", Expert Opinion Pharmacother. Jan. 12, 2011(1):73-84. doi: 10.1517/14656566.2010.516252. Epub Dec. 1, 2010.
Svennerholm L, et al., "A procedure for the quantitative isolation of brain gangliosides" Biochim Biophys Acta. Jan. 1980 18;617(1):97-109.
Tatituri RV, et al., "Inactivation of Corynebacterium glutamicum NCgl0452 and the role of MgtA in the biosynthesis of a novel mannosylated glycolipid involved in lipomannan biosynthesis", J Biol Chem. Feb. 2007 16;282(7):4561-72. Epub Dec. 19, 2006.
Zhang et al., "Suppression of human prostate tumor growth by a unique porstate-specific monoclonal antibody F77 targeting a glycolipid marker", PNAS, Jan. 12, 2010 107(2), 732-737.

* cited by examiner

*Primary Examiner* — Brad Duffy
*Assistant Examiner* — Nelson B Moseley, II
(74) *Attorney, Agent, or Firm* — Baker & Hostetler LLP

(57) ABSTRACT

Disclosed herein are antibodies that detect a lipid-like antigen on prostate cancer cells and methods of detecting and treating prostate cancer using the same.

1 Claim, 12 Drawing Sheets

Reactivity of F77 with human tissue and cancer cell lines

| Tissue | Immunohistology | Cell Line | Flow cytometry (fluorescent intensity) |
|---|---|---|---|
| Prostate | Carcinoma | PC3 | 118.71±2.99 |
| | -Strong stain | PC3-MM2 | 140.54±3.33 |
| | Normal duct | Du145 | 117.66±3.73 |
| | -Uneven stain | LNCaP | 92.96±4.03 |
| Breast | Carcinoma | SKBR3 | - |
| | -Slight background | BT474 | - |
| | Normal duct | MCF7 | 15.08±2.36 |
| | -Slight background | MB231 | 14.96±3.62 |
| | | HSQ-584 | - |
| Colon | Negative | SW260 | 12.26±2.7 |
| | | HT-135 | - |
| Kidney | Negative | Pasteur | - |
| | | HEK293T | - |
| Cervix | Negative | Hela | - |
| Pancreas | Negative | AsPC1 | - |
| | | BxPC3 | 13.90±2.86 |
| Bone | Negative | MG63 | - |
| | | U2OS | - |
| Brain | Small vessel | U87MG | - |
| Retina | Negative | ARPE19 | - |
| Lung | Negative | A549 | - |
| Skin | Negative | A431 | - |
| | | H130M | - |
| | | S85A | - |
| | | G361 | - |
| Blood | Negative | CEM (T cell) | - |
| | | Jurkat (T cell) | - |
| | | HL-60 (AML) | - |
| | | U937 (Monocyte) | - |
| | | SB (B cell) | - |
| Ovary | Negative | McDonald | 14.93±2.62 |
| | | OVCA4 | 16.39±3.17 |

FIGURE 2

| Tumor formation of prostate cancer subpopulations in nude mice ||||
| --- | --- | --- | --- |
| Cell subpopulation | No. of mice with palpable tumors | Average time to tumor formation (days) | Average tumor size (mm$^3$) |
| F77-/RWPE-1 | 1/6 | 40 | 21.87 |
| F77+/RWPE-1 | 4/6 | 31($\pm$7) | 59.51$\pm$8.16 |
| RWPE-2 | 4/6 | 23($\pm$8) | 49.15$\pm$6.18 |

FIGURE 5

FIG. 6A
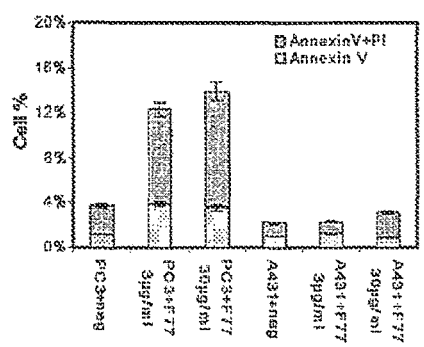
FIG. 6B
FIG. 6C
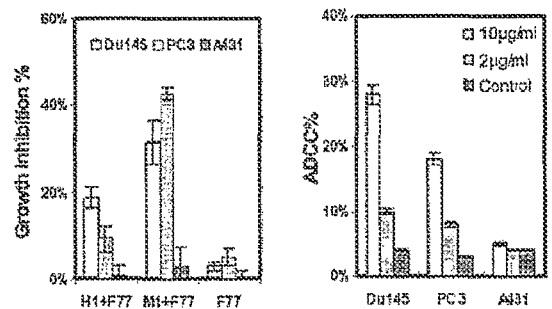

SEQUENCE LISTING

```
<160> NUMBER OF SEQ ID NOS: 92

<210> SEQ ID NO 1
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Thr Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Tyr Thr Phe Thr Ile
65                  70                  75                  80

Ser Ser Leu Gln Pro Glu Asp Ile Ala Thr Tyr Tyr Cys Ser Gln Gly
                85                  90                  95

Thr His Ala Pro Phe Thr Phe Gly Gln Gly Thr Lys Val Glu Ile Lys
                100                 105                 110

Arg
```

```
<210> SEQ ID NO 2
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Thr Leu Val His Ser
            20                  25                  30

Asn Gly Asn Thr Phe Leu Ala Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Tyr Thr Phe Thr Ile
65                  70                  75                  80

Ser Ser Leu Gln Pro Glu Asp Ile Ala Thr Tyr Tyr Cys Ser Gln Gly
                85                  90                  95

Thr His Ala Pro Phe Thr Phe Gly Gln Gly Thr Lys Val Glu Ile Lys
            100                 105                 110

Arg

<210> SEQ ID NO 3
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Thr Leu Val His Ser
            20                  25                  30

Asn Gly Asn Thr Phe Leu Val Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Tyr Thr Phe Thr Ile
65                  70                  75                  80

Ser Ser Leu Gln Pro Glu Asp Ile Ala Thr Tyr Tyr Cys Ser Gln Gly
                85                  90                  95

Thr His Ala Pro Phe Thr Phe Gly Gln Gly Thr Lys Val Glu Ile Lys
            100                 105                 110

Arg

<210> SEQ ID NO 4
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct
```

<400> SEQUENCE: 4

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Tyr Asn Ser Thr Leu Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 5

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Val Asn Ser Thr Leu Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 6
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 6

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Gly Arg Gly Leu Glu Trp Ile
            35                  40                  45

Gly Ile Ile Trp Ala Gly Gly Asn Thr Asn Leu Asn Ser Thr Leu Lys
 50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 7

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Gly Arg Gly Leu Glu Trp Ile
            35                  40                  45

Gly Ile Ile Trp Ala Gly Gly Asn Thr Asn Ile Asn Ser Thr Leu Lys
 50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 8

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Gly Arg Gly Leu Glu Trp Ile
            35                  40                  45

Gly Ile Ile Trp Ala Gly Gly Asn Thr Asn Tyr Asn Ser Thr Gly Lys
 50                  55                  60

Ser Arg Ala Thr Met Leu Val Asp Thr Ser Lys Asn Gln Phe Ser Leu
65                  70                  75                  80

```
Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 9

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Tyr Asn Ser Thr Ala Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 10

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Tyr Asn Ser Thr Ser Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115
```

<210> SEQ ID NO 11
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 11

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Tyr Asn Ser Thr Thr Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 12
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 12

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Val Asn Ser Thr Gly Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 13

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Val Asn Ser Thr Ala Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 14
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 14

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Val Asn Ser Thr Ser Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 15

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

```
Gly Val His Trp Val Arg Gln Pro Gly Arg Gly Leu Glu Trp Ile
            35                  40                  45

Gly Ile Ile Trp Ala Gly Gly Asn Thr Asn Val Asn Ser Thr Thr Lys
 50                      55                  60

Ser Arg Ala Thr Met Leu Val Asp Thr Ser Lys Asn Gln Phe Ser Leu
 65                  70                  75                  80

Arg Leu Ser Ser Val Thr Ala Ala Asp Thr Ala Val Tyr Tyr Cys Ala
                 85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 16
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 16

Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Thr Phe Thr Tyr Tyr
            20                  25                  30

Gly Val His Trp Val Arg Gln Pro Gly Arg Gly Leu Glu Trp Ile
            35                  40                  45

Gly Ile Ile Trp Ala Gly Gly Asn Thr Asn Leu Asn Ser Thr Gly Lys
 50                      55                  60

Ser Arg Ala Thr Met Leu Val Asp Thr Ser Lys Asn Gln Phe Ser Leu
 65                  70                  75                  80

Arg Leu Ser Ser Val Thr Ala Ala Asp Thr Ala Val Tyr Tyr Cys Ala
                 85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 17
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 17

Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Thr Phe Thr Tyr Tyr
            20                  25                  30

Gly Val His Trp Val Arg Gln Pro Gly Arg Gly Leu Glu Trp Ile
            35                  40                  45

Gly Ile Ile Trp Ala Gly Gly Asn Thr Asn Leu Asn Ser Thr Ala Lys
 50                      55                  60

Ser Arg Ala Thr Met Leu Val Asp Thr Ser Lys Asn Gln Phe Ser Leu
 65                  70                  75                  80
```

-continued

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 18
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 18

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Leu Asn Ser Thr Ser Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 19
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 19

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Leu Asn Ser Thr Thr Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 20
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 20

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Ile Asn Ser Thr Gly Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 21
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 21

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Ile Asn Ser Thr Ala Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 22
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

```
<400> SEQUENCE: 22

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Ile Asn Ser Thr Ser Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 23
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 23

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Trp Ala Gly Gly Asn Thr Asn Ile Asn Ser Thr Thr Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 24
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 24

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30
```

-continued

```
Gly Val His Trp Val Arg Gln Pro Gly Arg Gly Leu Glu Trp Ile
            35                  40                  45

Gly Ile Ile Phe Ala Gly Gly Asn Thr Asn Tyr Asn Ser Thr Leu Lys
 50                  55                  60

Ser Arg Ala Thr Met Leu Val Asp Thr Ser Lys Asn Gln Phe Ser Leu
 65                  70                  75                  80

Arg Leu Ser Ser Val Thr Ala Ala Asp Thr Ala Val Tyr Tyr Cys Ala
                 85                  90                  95

Arg Asp Asp Tyr Ala Ala Met Asp Tyr Trp Gly Gln Gly Ser Leu Val
            100                 105                 110

Thr Val Ser Ser
            115
```

<210> SEQ ID NO 25
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 25

```
Gln Val Gln Leu Gln Glu Ser Gly Pro Gly Leu Val Arg Pro Ser Gln
  1               5                  10                  15

Thr Leu Ser Leu Thr Cys Thr Val Ser Gly Phe Thr Phe Thr Tyr Tyr
             20                  25                  30

Gly Val His Trp Val Arg Gln Pro Gly Arg Gly Leu Glu Trp Ile
            35                  40                  45

Gly Ile Ile Phe Ala Gly Gly Asn Thr Asn Val Asn Ser Thr Leu Lys
 50                  55                  60

Ser Arg Ala Thr Met Leu Val Asp Thr Ser Lys Asn Gln Phe Ser Leu
 65                  70                  75                  80

Arg Leu Ser Ser Val Thr Ala Ala Asp Thr Ala Val Tyr Tyr Cys Ala
                 85                  90                  95

Arg Asp Asp Tyr Ala Ala Met Asp Tyr Trp Gly Gln Gly Ser Leu Val
            100                 105                 110

Thr Val Ser Ser
            115
```

<210> SEQ ID NO 26
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 26

```
Gln Val Gln Leu Gln Glu Ser Gly Pro Gly Leu Val Arg Pro Ser Gln
  1               5                  10                  15

Thr Leu Ser Leu Thr Cys Thr Val Ser Gly Phe Thr Phe Thr Tyr Tyr
             20                  25                  30

Gly Val His Trp Val Arg Gln Pro Gly Arg Gly Leu Glu Trp Ile
            35                  40                  45

Gly Ile Ile Phe Ala Gly Gly Asn Thr Asn Leu Asn Ser Thr Leu Lys
 50                  55                  60

Ser Arg Ala Thr Met Leu Val Asp Thr Ser Lys Asn Gln Phe Ser Leu
 65                  70                  75                  80
```

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 27
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 27

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Ile Asn Ser Thr Leu Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 28
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 28

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Tyr Asn Ser Thr Gly Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

```
<210> SEQ ID NO 29
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 29

Gln Val Gln Leu Gln Glu Ser Gly Pro Gly Leu Val Arg Pro Ser Gln
1               5                  10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Tyr Asn Ser Thr Ala Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 30
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 30

Gln Val Gln Leu Gln Glu Ser Gly Pro Gly Leu Val Arg Pro Ser Gln
1               5                  10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Tyr Asn Ser Thr Ser Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 31
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct
```

-continued

```
<400> SEQUENCE: 31

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Tyr Asn Ser Thr Thr Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 32
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 32

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Val Asn Ser Thr Gly Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 33
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 33

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30
```

```
Gly Val His Trp Val Arg Gln Pro Gly Arg Gly Leu Glu Trp Ile
            35                  40                  45

Gly Ile Ile Phe Ala Gly Gly Asn Thr Asn Val Asn Ser Thr Ala Lys
 50                      55                  60

Ser Arg Ala Thr Met Leu Val Asp Thr Ser Lys Asn Gln Phe Ser Leu
 65                  70                  75                  80

Arg Leu Ser Ser Val Thr Ala Ala Asp Thr Ala Val Tyr Tyr Cys Ala
                 85                  90                  95

Arg Asp Asp Tyr Ala Ala Met Asp Tyr Trp Gly Gln Gly Ser Leu Val
                100                 105                 110

Thr Val Ser Ser
            115

<210> SEQ ID NO 34
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 34

Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Thr Phe Thr Tyr Tyr
                20                  25                  30

Gly Val His Trp Val Arg Gln Pro Gly Arg Gly Leu Glu Trp Ile
            35                  40                  45

Gly Ile Ile Phe Ala Gly Gly Asn Thr Asn Val Asn Ser Thr Ser Lys
 50                      55                  60

Ser Arg Ala Thr Met Leu Val Asp Thr Ser Lys Asn Gln Phe Ser Leu
 65                  70                  75                  80

Arg Leu Ser Ser Val Thr Ala Ala Asp Thr Ala Val Tyr Tyr Cys Ala
                 85                  90                  95

Arg Asp Asp Tyr Ala Ala Met Asp Tyr Trp Gly Gln Gly Ser Leu Val
                100                 105                 110

Thr Val Ser Ser
            115

<210> SEQ ID NO 35
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 35

Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Thr Phe Thr Tyr Tyr
                20                  25                  30

Gly Val His Trp Val Arg Gln Pro Gly Arg Gly Leu Glu Trp Ile
            35                  40                  45

Gly Ile Ile Phe Ala Gly Gly Asn Thr Asn Val Asn Ser Thr Thr Lys
 50                      55                  60

Ser Arg Ala Thr Met Leu Val Asp Thr Ser Lys Asn Gln Phe Ser Leu
 65                  70                  75                  80
```

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 36
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 36

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Leu Asn Ser Thr Gly Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 37
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 37

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Leu Asn Ser Thr Ala Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

-continued

```
<210> SEQ ID NO 38
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 38

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Leu Asn Ser Thr Ser Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 39
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 39

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Leu Asn Ser Thr Thr Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 40
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct
```

<400> SEQUENCE: 40

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Ile Asn Ser Thr Gly Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 41
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 41

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
        35                  40                  45

Gly Ile Ile Phe Ala Gly Gly Asn Thr Asn Ile Asn Ser Thr Ala Lys
    50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 42
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 42

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

```
Gly Val His Trp Val Arg Gln Pro Pro Gly Arg Gly Leu Glu Trp Ile
            35                  40                  45

Gly Ile Ile Phe Ala Gly Gly Asn Thr Asn Ile Asn Ser Thr Thr Lys
        50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 43
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 43

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Tyr Tyr
            20                  25                  30

Gly Val His Trp Val Arg Gln Pro Pro Gly Arg Gly Leu Glu Trp Ile
            35                  40                  45

Gly Ile Ile Phe Ala Gly Gly Asn Thr Asn Ile Asn Ser Thr Thr Lys
        50                  55                  60

Ser Arg Ala Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Asp Tyr Ala Ala Met Asp Tyr Trp Gly Gln Gly Ser Leu Val
            100                 105                 110

Thr Val Ser Ser
        115

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 44

Tyr Tyr Gly Val His
1               5

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct
```

```
<400> SEQUENCE: 45

Ile Ile Trp Ala Gly Gly Asn Thr Asn Tyr Asn Ser Thr Leu Lys Ser
1               5                   10                  15

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 46

Asp Asp Tyr Ala Ala Met Asp Tyr
1               5

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 47

Ile Ile Trp Ala Gly Gly Asn Thr Asn Val Asn Ser Thr Leu Lys Ser
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 48

Ile Ile Trp Ala Gly Gly Asn Thr Asn Leu Asn Ser Thr Leu Lys Ser
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 49

Ile Ile Trp Ala Gly Gly Asn Thr Asn Ile Asn Ser Thr Leu Lys Ser
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 50

Ile Ile Trp Ala Gly Gly Asn Thr Asn Tyr Asn Ser Thr Gly Lys Ser
1               5                   10                  15
```

```
<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 51

Ile Ile Trp Ala Gly Gly Asn Thr Asn Tyr Asn Ser Thr Ala Lys Ser
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 52

Ile Ile Trp Ala Gly Gly Asn Thr Asn Tyr Asn Ser Thr Ser Lys Ser
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 53

Ile Ile Trp Ala Gly Gly Asn Thr Asn Tyr Asn Ser Thr Thr Lys Ser
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 54

Ile Ile Trp Ala Gly Gly Asn Thr Asn Val Asn Ser Thr Gly Lys Ser
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 55

Ile Ile Trp Ala Gly Gly Asn Thr Asn Val Asn Ser Thr Ala Lys Ser
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct
```

```
<400> SEQUENCE: 56

Ile Ile Trp Ala Gly Gly Asn Thr Asn Leu Asn Ser Thr Ser Lys Ser
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 57

Ile Ile Trp Ala Gly Gly Asn Thr Asn Leu Asn Ser Thr Thr Lys Ser
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 58

Ile Ile Trp Ala Gly Gly Asn Thr Asn Ile Asn Ser Thr Gly Lys Ser
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 59

Ile Ile Trp Ala Gly Gly Asn Thr Asn Ile Asn Ser Thr Ala Lys Ser
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 60

Ile Ile Trp Ala Gly Gly Asn Thr Asn Ile Asn Ser Thr Ser Lys Ser
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 61

Ile Ile Trp Ala Gly Gly Asn Thr Asn Ile Asn Ser Thr Thr Lys Ser
1               5                   10                  15
```

```
<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 62

Ile Ile Phe Ala Gly Gly Asn Thr Asn Tyr Asn Ser Thr Leu Lys Ser
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 63

Ile Ile Phe Ala Gly Gly Asn Thr Asn Val Asn Ser Thr Leu Lys Ser
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 64

Ile Ile Phe Ala Gly Gly Asn Thr Asn Leu Asn Ser Thr Leu Lys Ser
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 65

Ile Ile Phe Ala Gly Gly Asn Thr Asn Ile Asn Ser Thr Leu Lys Ser
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 66

Ile Ile Phe Ala Gly Gly Asn Thr Asn Tyr Asn Ser Thr Gly Lys Ser
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct
```

```
<400> SEQUENCE: 67

Ile Ile Phe Ala Gly Gly Asn Thr Asn Tyr Asn Ser Thr Ala Lys Ser
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 68

Ile Ile Phe Ala Gly Gly Asn Thr Asn Tyr Asn Ser Thr Ser Lys Ser
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 69

Ile Ile Phe Ala Gly Gly Asn Thr Asn Tyr Asn Ser Thr Thr Lys Ser
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 70

Ile Ile Phe Ala Gly Gly Asn Thr Asn Val Asn Ser Thr Gly Lys Ser
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 71

Ile Ile Phe Ala Gly Gly Asn Thr Asn Val Asn Ser Thr Ala Lys Ser
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 72

Ile Ile Phe Ala Gly Gly Asn Thr Asn Val Asn Ser Thr Ser Lys Ser
1               5                   10                  15
```

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 73

Ile Ile Phe Ala Gly Gly Asn Thr Asn Val Asn Ser Thr Thr Lys Ser
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 74

Ile Ile Phe Ala Gly Gly Asn Thr Asn Leu Asn Ser Thr Gly Lys Ser
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 75

Ile Ile Phe Ala Gly Gly Asn Thr Asn Leu Asn Ser Thr Ala Lys Ser
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 76

Ile Ile Phe Ala Gly Gly Asn Thr Asn Leu Asn Ser Thr Ser Lys Ser
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 77

Ile Ile Phe Ala Gly Gly Asn Thr Asn Leu Asn Ser Thr Thr Lys Ser
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic peptide construct

```
<400> SEQUENCE: 78

Ile Ile Phe Ala Gly Gly Asn Thr Asn Ile Asn Ser Thr Gly Lys Ser
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 79

Ile Ile Phe Ala Gly Gly Asn Thr Asn Ile Asn Ser Thr Ala Lys Ser
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 80

Ile Ile Phe Ala Gly Gly Asn Thr Asn Ile Asn Ser Thr Ser Lys Ser
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 81

Ile Ile Phe Ala Gly Gly Asn Thr Asn Ile Asn Ser Thr Thr Lys Ser
1               5                   10                  15

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 82

Lys Val Ser Asn Arg Phe Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 83

Ser Gln Gly Thr His Ala Pro Phe Thr
1               5
```

```
<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 84

Cys Arg Ser Ser Gln Thr Leu Val His Ser Asn Gly Asn Thr Phe Leu
1               5                   10                  15

His

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 85

Cys Arg Ser Ser Gln Thr Leu Val His Ser Asn Gly Asn Thr Phe Leu
1               5                   10                  15

Ala

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 86

Cys Arg Ser Ser Gln Thr Leu Val His Ser Asn Gly Asn Thr Phe Leu
1               5                   10                  15

Val

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)..(17)
<223> OTHER INFORMATION: His, Ala or Val

<400> SEQUENCE: 87

Cys Arg Ser Ser Gln Thr Leu Val His Ser Asn Gly Asn Thr Phe Leu
1               5                   10                  15

Xaa

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (3)..(3)
<223> OTHER INFORMATION: Trp or Phe
```

```
<220> FEATURE:
<221> NAME/KEY: MOD_RES
<222> LOCATION: (10)..(10)
<223> OTHER INFORMATION: Tyr, Val, Leu or Ile
<220> FEATURE:
<221> NAME/KEY: MOD_RES
<222> LOCATION: (14)..(14)
<223> OTHER INFORMATION: Leu, Gly, Ala, Ser or Thr

<400> SEQUENCE: 88

Ile Ile Xaa Ala Gly Gly Asn Thr Asn Xaa Asn Ser Thr Xaa Lys Ser
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 89

Ile Ile Trp Ala Gly Gly Asn Thr Asn Val Asn Ser Thr Ser Lys Ser
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 90

Ile Ile Trp Ala Gly Gly Asn Thr Asn Val Asn Ser Thr Thr Lys Ser
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 91

Ile Ile Trp Ala Gly Gly Asn Thr Asn Leu Asn Ser Thr Gly Lys Ser
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 92

Ile Ile Trp Ala Gly Gly Asn Thr Asn Leu Asn Ser Thr Ala Lys Ser
1               5                   10                  15
```

ANTI-PROSTATE CANCER ANTIBODIES AND METHODS OF DETECTION AND TREATMENT OF PROSTATE CANCER USING THE SAME

CROSS-REFERENCE TO RELATED APPLICATIONS

This application is a continuation of U.S. patent application Ser. No. 13/516,305, filed on Oct. 25, 2012, which is a National Stage of International Application No. PCT/US2010/060782, filed Dec. 16, 2010, which claims the benefit of U.S. Provisional Application No. 61/287,063, filed Dec. 16, 2009, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jul. 18, 2014, is named Sequence_Listing_CRF 103241-005956 and is 64,412 bytes in size.

TECHNICAL FIELD

The subject matter described herein relates to the field of molecular biology and immunology. More specifically, the subject matter relates to immunotherapeutics, including antibodies that detect prostate cancer and methods for using such antibodies to treat subjects in need of such treatment.

BACKGROUND

Prostate cancer is the second leading cause of cancer-related death in men in the United States. Studies indicate that 30-45% of patients with clinically localized disease are found with Stage T3. These patients have extra-capsular extension, where prostate cancer cells have extended into or beyond the outer lining of the prostate gland. In these patients, cancer may relapse and metastasize after local therapy.

In fact, a large percentage of androgen-independent prostatic carcinomas metastasize to bone. These metastases are difficult to treat and contribute to increased morbidity and mortality, with a median survival of approximately a year after diagnosis.

Despite the effectiveness of hormone therapy, most patients with metastatic disease eventually progress to an androgen-independent state at which time the disease is incurable with a median survival rate of 1 year. Overall, the 5-year survival rate for metastatic prostate cancer is only 34%. New diagnostic, prognostic, and therapeutic approaches are clearly needed for the treatment of advanced and metastatic prostate cancer.

One approach is antibody therapy. However, the antibodies currently available for detection and treatment of prostate cancers are limited. The MAb 7E11-05.3, which binds to Prostate-Specific Membrane Antigen (PSMA), has been developed for clinical trials. The ProstaScint® scan (Cytogen, Princeton, N.J.), based on Indium-111 labeled 7E11-05.3, appears superior to the conventional imaging methods for soft-tissue disease, but has limitations because it binds to the intracellular domain on PSMA. In addition, PMSA is not expressed in certain advanced, androgen-independent tumor cells such as PC3 and Du145, and therefore this antibody is not useful for imaging bone metastases. Recent studies show that the anti-prostate stem cell antigen (PSCA) MAb1G8 can inhibit tumor growth of androgen-dependent tumor xenografts. However, anti-PSCA MAbs are ineffective against androgen-independent PC3 tumors, which do not express PSCA. An analysis of prostate cancer tissue sections demonstrated that PSCA is absent in about 20% of specimens. Therefore, defining new prostate specific markers is important in order to improve the diagnosis and treatment of advanced androgen-independent prostate cancer.

SUMMARY

Described herein are antibodies that detect a novel glycolipid-like antigen, "PCLA," or "Prostate Cancer Lipid-like Antigen." PCLA is highly restricted to prostate cancer cell and prostasome surfaces. In one embodiment, the anti-PCLA antibody is the F77 MAb, a mouse monoclonal antibody as described in Carroll, A M, et al., 1984, Sury Synth Path Res., 3, 189-200 and Carroll, A M, et al., 1984, Clin Inununol Immunopath, 33, 268-281, each of which is incorporated by reference herein.

Described herein are the amino acid sequences of the variable regions of the MAb, a light chain variable region having the amino acid sequence of SEQ ID NO:1 or a heavy chain variable region having the amino acid sequence of SEQ ID NO:4.

Disclosed herein are novel antibodies. Included are antibody or antibody functional fragments (other than F77 MAb) that bind to B-III dodecaosylceramide or B-IV tetradecaosylceramide. In further embodiments are included antibody or antibody functional fragments that compete for binding with F77 MAb. In further embodiments are included antibody or antibody functional fragments that compete for binding with F77 MAb to B-III dodecaosylceramidc and/or B-IV tetradecaosylceramide. In some embodiments the antibody or antibody functional fragments comprise CDRs of the heavy chain or light chain variable region, Fab, F(ab')$_2$, Fd, Fabc, Fv or Sc. In some embodiments the antibody or antibody functional fragments are humanized. In some embodiments the antibody or antibody functional fragment is conjugated to a toxin or cytotoxic agent. Also provided are methods of detecting the degree of differentiation of prostate cancer comprising contacting a sample of prostatic tissue with the antibody or antibody functional fragment of any one of the preceding embodiments, and correlating the amount of binding of the antibody to the sample with the degree of differentiation. Also provided are methods of determining the degree of differentiation of prostate cancer comprising contacting prostasomes with the antibody or antibody functional fragment of any one of the preceding embodiments and correlating the amount of binding of the antibody to the prostasomes with the degree of differentiation. Also provided are methods of treating a subject having prostate cancer comprising assaying the degree of differentiation of the cancer and in response treating with an effective amount of the antibody or antibody functional fragment of any one of the preceding embodiments. Also provided are methods of preferentially inducing cell death in primary or metastatic prostate cancer cells over non-cancerous prostate cells in a human, comprising administering the antibody or antibody functional fragment of any one of the preceding embodiments. Also provided are methods of inhibiting prostate tumor growth in a patient having said tumor comprising administering the antibody or antibody functional fragment of any one of the preceding embodiments. Also provided are methods of treating a subject having prostate cancer comprising administering the antibody or antibody functional fragment of any one of the preceding embodiments in combination with additional anti-cancer treatments, including chemotherapy, androgen deprivation therapy, and radiation therapy, alone or in combination.

Included are antibodies that compete for binding with an antibody comprising a light chain variable region comprising the amino acid sequence of, or substantially similar to, SEQ ID NO:1, or the CDRs thereof, or a heavy chain variable region comprising the amino acid sequence of, or substantially similar to, SEQ ID NO:4, or the CDRs thereof. Further embodiments include antibodies that compete for binding with an antibody comprising a light chain variable region having the amino acid sequence of, or substantially similar to, SEQ ID NO:1, or the CDRs thereof; or comprising a heavy chain variable region having the amino acid sequence of, or substantially similar to, SEQ ID NO:4, or the CDRs thereof.

Described herein are novel antibodies comprising any combination of the following CDR sequences:

```
                                              (SEQ ID NO: 87)
Light chain CDR1 = C-R-S-S-Q-T-L-V-H-S-N-G-N-T-F-L-
(H/A/V) (i.e. the last residue can be either
H, A or V)

(SEQ ID NO: 82)
Light chain CDR2 = K-V-S-N-R-F-S (SEQ ID NO: 83)
Light chain CDR3 = S-Q-G-T-H-A-P-F-T (SEQ ID NO: 44)
Heavy chain CDR1: Y-Y-G-V-H (SEQ ID NO: 88)
Heavy chain CDR2: I-I-(W/F)-A-G-G-N-T-N-(Y/V/L/I)-
N-S-T-(L/G/A/S/T)-K-S (SEQ ID NO: 46)
Heavy chain CDR3: D-D-Y-A-A-M-D-Y
```

Described herein is an antibody comprising a light chain variable region having the amino acid sequence of, or substantially similar to, SEQ ID NO: 2 or 3. A further embodiment is an antibody comprising a heavy chain variable region having the amino acid sequence of, or substantially similar to, SEQ ID NOs: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43. A further embodiment is an antibody comprising a light chain variable region having the amino acid sequence of, or substantially similar to, SEQ ID NO: 2 or 3 and a heavy chain variable region having the amino acid sequence of, or substantially similar to, SEQ ID NOs: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43.

Described herein are antibodies or functional fragments thereof that are derived from any of the anti-PCLA antibodies described above. A further embodiment is a functional fragment of an antibody that comprises an amino acid sequence that is identical to, or substantially similar to, SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43, or the CDRs thereof. A further embodiment is a humanized antibody or functional fragment of any of the anti-PCLA antibodies described above, comprising one or more amino acid sequences as set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43, or the CDRs thereof. A further embodiment is a humanized antibody or functional fragment of any of the anti-PCLA antibodies described above, having one or more amino acid sequences as set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43, or the CDRs thereof.

Other embodiments include the polynucleotide sequences encoding an anti-PCLA antibody or functional fragment thereof that comprises at least one of the amino acid sequences as set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43, or a humanized antibody or CDR derived therefrom, or polynucleotide or amino acid sequences that are substantially similar thereto. Other embodiments include the polynucleotide sequences encoding an anti-PCLA antibody or functional fragment thereof that have at least one of the amino acid sequences as set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43, or a humanized antibody or CDR derived therefrom, or polynucleotide or amino acid sequences that are substantially similar thereto.

In some embodiments, antibodies or antigen-binding fragments can include a heavy chain CDR1 amino acid sequence substantially the same as, or identical to YYGVH (SEQ ID NO: 44). In some embodiments, antibodies or antigen-binding fragments can include a heavy chain CDR2 amino acid sequence substantially the same as, or identical to HWAGGNTNYNSTLKS (SEQ ID NO: 45). In some embodiments, antibodies or antigen-binding fragments can include a heavy chain CDR2 amino acid sequence substantially the same as, or identical to IIWAGGNTNVNSTLKS (SEQ ID NO: 47). In some embodiments, antibodies or antigen-binding fragments can include a heavy chain CDR2 amino acid sequence substantially the same as, or identical to IIWAGGNTNLNSTLKS (SEQ ID NO: 48). In some embodiments, antibodies or antigen-binding fragments can include a heavy chain CDR2 amino acid sequence substantially the same as, or identical to HWAGGNTNYNSTLKS (SEQ ID NO: 49). In some embodiments, antibodies or antigen-binding fragments can include a heavy chain CDR2 amino acid sequence substantially the same as, or identical to IIWAGGNTNYNSTGKS (SEQ ID NO: 50). In some embodiments, antibodies or antigen-binding fragments can include a heavy chain CDR2 amino acid sequence substantially the same as, or identical to HWAGGNTNYNSTAKS (SEQ ID NO: 51). In some embodiments, antibodies or antigen-binding fragments can include a heavy chain CDR2 amino acid sequence substantially the same as, or identical to IIWAGGNTNYNSTSKS (SEQ ID NO: 52). In some embodiments, antibodies or antigen-binding fragments can include a heavy chain CDR2 amino acid sequence substantially the same as, or identical to IIWAGGNTNYNSTTKS (SEQ ID NO: 53). In some embodiments, antibodies or antigen-binding fragments can include a heavy chain CDR2 amino acid sequence substantially the same as, or identical to IIWAGGNTNVNSTGKS (SEQ ID NO: 54). In some embodiments, antibodies or antigen-binding fragments can include a heavy chain CDR2 amino acid sequence substantially the same as, or identical to IIWAGGNTNVNSTGKS (SEQ ID NO: 55). In some embodiments, antibodies or antigen-binding fragments can include a heavy chain CDR2 amino acid sequence substantially the same as, or identical to IIWAGGNTNLNSTSKS (SEQ ID NO: 56). In some embodiments, antibodies or antigen-binding fragments can include a heavy chain CDR2 amino acid sequence substantially the same as, or identical to IIWAGGNTNLNSTTKS (SEQ ID NO: 57). In some embodiments, antibodies or antigen-binding fragments can include a heavy chain CDR2 amino acid sequence substantially the same as, or identical to IIWAGGNTNINSTGKS (SEQ ID NO: 58). In some embodiments, antibodies or antigen-binding fragments can include a heavy chain CDR2 amino acid sequence substantially the same as, or identical to IFWAGGNTNINSTAKS (SEQ ID NO: 59). In some embodiments, antibodies or antigen-binding fragments can include a heavy chain CDR2 amino acid sequence substantially the same as, or identical to IIWAGGNTNYNSTSKS (SEQ ID NO: 60). In some embodiments, antibodies or antigen-binding fragments can include a heavy chain CDR2 amino acid sequence substantially the same as, or identical to PIWAGGNTNINSTTKS (SEQ ID NO: 61). In some embodiments, antibodies or antigen-binding fragments can include a heavy chain CDR2 amino acid sequence substantially the same as, or identical to IIFAGGNTNLNSTLKS (SEQ ID NO: 62). In some embodiments, antibodies or antigen-binding fragments can include a heavy chain CDR2 amino acid sequence substantially the same as, or identical to IIFAGGNTNLNSTLKS (SEQ ID NO: 63). In some embodiments, antibodies or antigen-binding fragments can include a heavy chain CDR2 amino acid sequence substantially the same as, or identical to IIFAGGNTNLNSTLKS (SEQ ID NO: 64). In some embodiments, antibodies or antigen-binding fragments can include a heavy chain CDR2 amino acid sequence substantially the same as, or identical to IIFAGGNTNINSTLKS (SEQ ID NO: 65). In some embodiments, antibodies or antigen-binding fragments can include a heavy chain CDR2 amino acid sequence substantially the same as, or identical to ITFAGGNTNYNSTGKS (SEQ ID NO: 66). In some embodiments, antibodies or antigen-binding fragments can include a heavy chain CDR2 amino acid sequence substantially the same as, or identical to IIFAGGNTNVNSTAKS (SEQ ID NO: 67). In some embodiments, antibodies or antigen-binding fragments can include a heavy chain CDR2 amino acid sequence substantially the same as, or identical to HFAGGNTNYNSTSKS (SEQ ID NO: 68). In some embodiments, antibodies or antigen-binding fragments can include a heavy chain CDR2 amino acid sequence substantially the same as, or identical to IIFAGGNTNYNSTTKS (SEQ ID NO: 69). In some embodiments, antibodies or antigen-binding fragments can include a heavy chain CDR2 amino acid sequence substantially the same as, or identical to IIWAGGNTNLNSTGKS (SEQ ID NO: 89). In some embodiments, antibodies or antigen-binding fragments can include a heavy chain CDR2 amino acid sequence substantially the same as, or identical to IIWAGGNTNVNSTTKS (SEQ ID NO: 90). In some embodiments, antibodies or antigen-binding fragments can include a heavy chain CDR2 amino acid sequence substantially the same as, or identical to IIWAGGNTNLNSTGKS (SEQ ID NO: 91). In some embodiments, antibodies or antigen-binding fragments can include a heavy chain CDR2 amino acid sequence substantially the same as, or identical to IIWAGGNTNLNSTAKS (SEQ ID NO: 92).

In some embodiments, antibodies or antigen-binding fragments can include a heavy chain CDR2 amino acid sequence substantially the same as, or identical to IIFAGGNTNVNSTGKS (SEQ ID NO: 70). In some embodiments, antibodies or antigen-binding fragments can include a heavy chain CDR2 amino acid sequence substantially the same as, or identical to IIFAGGNTNVNSTAKS (SEQ ID NO: 71). In some embodiments, antibodies or antigen-binding fragments can include a heavy chain CDR2 amino acid sequence substantially the same as, or identical to IIFAGGNTNVNSTSKS (SEQ ID NO: 72). In some embodiments, antibodies or antigen-binding fragments can include a heavy chain CDR2 amino acid sequence substantially the same as, or identical to ITAGGNTNVNSTTKS (SEQ ID NO: 73). In some embodiments, antibodies or antigen-binding fragments can include a heavy chain CDR2 amino acid sequence substantially the same as, or identical to IIFAGGNTNLNSTGKS (SEQ ID NO: 74). In some embodiments, antibodies or antigen-binding fragments can include a heavy chain CDR2 amino acid sequence substantially the same as, or identical to IIFAGGNTNLNSTGKS (SEQ ID NO: 75).

In some embodiments, antibodies or antigen-binding fragments can include a heavy chain CDR2 amino acid sequence substantially the same as, or identical to IIFAGGNTNLNSTSKS (SEQ ID NO: 76). In some embodiments, antibodies or antigen-binding fragments can include a heavy chain CDR2 amino acid sequence substantially the same as, or identical to IIFAGGNTNLNSTTKS (SEQ ID NO: 77). In some embodiments, antibodies or antigen-binding fragments can include a heavy chain CDR2 amino acid sequence substantially the same as, or identical to IIFAGGNTNINSTGKS (SEQ ID NO: 78). In some embodiments, antibodies or antigen-binding fragments can include a heavy chain CDR2 amino acid sequence substantially the same as, or identical to IIFAGGNTNINSTAKS (SEQ ID NO: 79). In some embodiments, antibodies or antigen-binding fragments can include a heavy chain CDR2 amino acid sequence substantially the same as, or identical to IIFAGGNTNINSTGKS (SEQ ID NO: 80). In some embodiments, antibodies or antigen-binding fragments can include a heavy chain CDR2 amino acid sequence substantially the same as, or identical to IIFAGGNTNINSTTKS (SEQ ID NO: 81).

In some embodiments, antibodies or antigen-binding fragments can include a heavy chain CDR3 amino acid sequence substantially the same as, or identical to DDYAAMDY (SEQ ID NO: 46).

In some embodiments, antibodies or antigen-binding fragments can include a light chain CDR1 amino acid sequence substantially the same as, or identical to CRSSQTLVHSNGNTFLH (SEQ ID NO: 84).

In some embodiments, antibodies or antigen-binding fragments can include a light chain CDR1 amino acid sequence substantially the same as, or identical to CRSSQTLVHSNGNTFLA (SEQ ID NO: 85). In some embodiments, antibodies or antigen-binding fragments can include a light chain CDR1 amino acid sequence substantially the same as, or identical to CRSSQTLVHSNGNTFLV (SEQ ID NO: 86). In some embodiments, antibodies or antigen-binding fragments can include a light chain CDR2 amino acid sequence substantially the same as, or identical to KVSNRFS (SEQ ID NO: 82). In some embodiments, antibodies or antigen-binding fragments can include a light chain CDR2 amino acid sequence substantially the same as, or identical to SQGTHAPFT (SEQ ID NO: 83).

Described herein are complexes comprising any of the anti-prostate cancer antibodies described above, including antibodies and functional fragments derived therefrom, bound to PCLA. Further embodiments include complexes wherein the PCLA is on human prostasomes. Further embodiments include complexes wherein the PCLA is on metastatic or androgen independent human prostatic cancer tissue.

Described herein are vectors or cells comprising one or more such polynucleotide sequences.

Described herein are kits comprising the antibodies, functional fragments, or humanized or derived antibodies. Further embodiments include kits comprising the polynucleotides encoding the antibodies, functional fragments, or humanized or derived antibodies.

Described herein are novel methods of detecting and treating prostate cancer with any of the anti-prostate cancer antibodies described above, including MAb F77 and the novel antibodies and/or novel functional fragments derived therefrom, either as a sole treatment or in combination with additional anti-cancer treatments, including chemotherapy, androgen deprivation therapy, and radiation therapy, alone or in combination. See Dal Pra, A. et al. Current Oncology 17:28-38 (2010), Foley, R. et al. Prostate (Oct. 13, 2010), Sumey, C. et al. Expert Opinion Pharmacother. 12:73-84 (2011), which are hereby incorporated by reference in their entirety and for all purposes. Described herein are methods of detecting and treating prostate cancer with any of the anti-PCLA antibodies described above, including antibodies and functional fragments derived therefrom. Described herein are methods of detecting and treating prostate cancer with any of the anti-F77 cancer antibodies described above, including antibodies and functional fragments derived therefrom.

Described herein are methods of detecting the degree of differentiation of prostate cancer comprising contacting a sample of prostatic tissue with an anti-PCLA antibody and correlating the amount of binding of said antibody to said sample with said degree of differentiation. Further embodiments include the method of detecting the degree of differentiation of prostate cancer wherein the cancer is androgen independent. Further embodiments include the method of detecting the degree of differentiation of prostate cancer wherein the cancer is metastatic. Further embodiments include the method of detecting the degree of differentiation of prostate cancer in a prostatic tissue sample wherein the sample is human. Further embodiments include the method of detecting wherein the absence or degree of differentiation of prostate cancer is measured using a CDR, Fab, ScFv, or functional fragment of an anti-PCLA antibody. Further embodiments include the method of detecting the degree of differentiation of prostate cancer wherein the anti-PCLA antibody comprises at least one of a variable light chain nucleic acid sequence as set forth in SEQ ID NO:1 or a variable light chain nucleic acid sequence as set forth in SEQ ID NO:4.

Described herein are methods of determining the degree of differentiation of prostate cancer comprising contacting prostasomes with an anti-PCLA antibody and correlating the amount of binding of said antibody to said prostasomes with said degree of differentiation. Further embodiments include the methods of determining the degree of differentiation of prostate cancer comprising contacting prostasomes with an anti-PCLA antibody and correlating the amount of binding of said antibody to said prostasomes with said degree of differentiation wherein the prostasomes comprise semen or serum.

Described herein are methods for treating or preventing a PCLA associated disease a subject in need of such treatment. In one embodiment, the PCLA associated disease is prostate cancer. The methods comprise administering to the subject an antibody or antigen-binding fragment that specifically binds to PCLA in an amount effective to treat or prevent the PCLA associated disease. In some embodiments the methods comprise administering a pharmaceutical composition including an antibody or antigen-binding fragment and a pharmaceutically acceptable carrier.

Described herein are methods of treating a subject having prostate cancer comprising assaying the degree of differentiation of said cancer and in response treating with an effective amount of an anti-PCLA antibody.

Embodiments of each of the methods described herein include methods wherein the antibody is a humanized antibody, CDR, Fab, ScFv, or functional fragment thereof.

Embodiments of each of the methods described herein include methods wherein the prostate cancer is androgen independent. Embodiments of each of the methods described herein include methods wherein wherein the prostate cancer is androgen dependent. Embodiments of each of the methods described herein include methods wherein the prostate cancer is metastatic. Embodiments of each of the methods described herein include methods wherein the prostate cancer is primary.

Embodiments of each of the methods comprising detecting or treating metastatic prostate cancer include methods wherein the metastatis is present in bone. Further embodiments of each of the methods comprising detecting or treating metastatic prostate cancer include methods wherein the metastatic prostate cancer is present in the brain.

Described herein are methods of preferentially inducing cell death in primary or metastatic prostate cancer cells over non-cancerous prostate cells in a human, comprising administering a humanized antibody CDR, Fab, ScFv, or functional fragment thereof derived from the antibody having a variable light chain sequence as set forth in SEQ ID NO:1, or the CDRs thereof, and a variable heavy chain sequence as set forth in SEQ ID NO:4, or the CDRs thereof. A further embodiment includes methods of preferentially inducing cell death in primary or metastatic prostate cancer cells over non-cancerous prostate cells in a human, comprising administering a humanized antibody, or an Fab, ScFv, or functional fragment thereof comprising a variable light chain sequence as set forth in SEQ ID NOs: 1, 2, or 3, or the CDRs thereof. Further embodiments include methods of preferentially inducing cell death in primary or metastatic prostate cancer cells over non-cancerous prostate cells in a human, comprising administering a humanized antibody, Fab, ScFv, or functional fragment thereof comprising a variable heavy chain sequence as set forth in one of SEQ ID NOs: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43, or the CDRs thereof. Further embodiments include methods of preferentially inducing cell death in primary or metastatic prostate cancer cells over non-cancerous prostate cells in a human, comprising administering a humanized CDR derived from an antibody comprising a sequence as set forth in SEQ ID NOs: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43, or the CDRs thereof. Further embodiments include methods of preferentially inducing cell death in primary or metastatic prostate cancer cells over non-cancerous prostate cells in a human, comprising administering a humanized CDR derived from an antibody having a sequence as set forth in SEQ ID NO:s 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43, or the CDRs thereof. Further embodiments include methods of preferentially inducing cell death in primary or metastatic prostate cancer cells over non-cancerous prostate cells in a human, wherein said cell death is induced via antibody dependent cellular cytotoxicity or complement-dependent cytotoxicity.

Described herein are methods of inhibiting prostate tumor growth in a patient having said tumor comprising administering a humanized antibody CDR, Fab, ScFv, or functional fragment thereof derived from the antibody having a variable light chain sequence as set forth in SEQ ID NO:1, or the CDRs thereof, and a variable heavy chain sequence as set forth in SEQ ID NO:4, or the CDRs thereof.

Described herein are any of the antibodies described herein further bound to PCLA. Further embodiments include any of the antibodies described herein bound to PCLA on human prostasomes. Further embodiments include any of the antibodies described herein bound to, wherein the PCLA is on metastatic or androgen independent human prostatic cancer tissue.

BRIEF DESCRIPTION OF THE DRAWINGS

FIG. 2 is a table listing the relative reactivity of F77 MAb with human tissue and cancer cell lines as determined by immunohistochemical staining and fluorescence of cells bound by F77 MAb using flow cytometry, respectively.

FIG. 5 is a table summarizing the results of tumor formation of the RWPE prostate cancer subpopulations in nude mice, showing tumor formation in mice injected with the RWPE-1 prostate cancer cell subpopulation that binds F77 MAb (F77+/RWPE-1), and a very low incidence of small tumor formation in mice injected with the RWPE-1 prostate cancer cell subpopulation that does not bind F77 MAb (F77−/RWPE-1).

FIG. 6A is a bar graph plotting the results of Annexin V and propidium iodide staining demonstrating that MAb F77 induces apoptosis in a percentage of A431 and PC3 cells treated with 3 μg/ml or 30 μg/ml MAb F77 for 4 hours at 37° C. Negative controls (neg) are cells treated with a negative control (irrelevant) murine IgG3 MAb. Data expressed as mean±SD of triplicate measurements.

FIG. 6B is a bar graph plotting percent growth inhibition of F77 MAb exposed, as determined using an MTT assay, indicating that the F77 MAb initiates complement dependent cytotoxity in prostate cancer cells in the presence of serum. (H1+F77: 25 μg/ml MAb F77 in 100 μl medium containing 1% human serum; M1+F77: 25 μg/ml MAb F77 in 100 μl medium containing 1% mouse serum; F77: 25 μg/ml F77 MAb in 100 μl serum free medium; Data expressed as mean±SD of triplicate measurements.)

FIG. 6C is a bar graph depicting the results of an ADCC assay wherein PC3 or Du145 target cells were treated with negative control (irrelevant) murine IgG3 MAb (0) or MAb F77 (2 and 10 μg/ml, respectively) and exposed to effector cells (monocyte-like U937 cells) at an effector: target cell ratio of 2:1. A431 cells were used as control cells. ADCC % was calculated following the manufacturer's instructions for the CytoTox 96© Non-Radioactive Cytotoxicity Assay (Promega). Data expressed as mean±SD of triplicate measurements.

DETAILED DESCRIPTION OF ILLUSTRATIVE EMBODIMENTS

Figure 1:
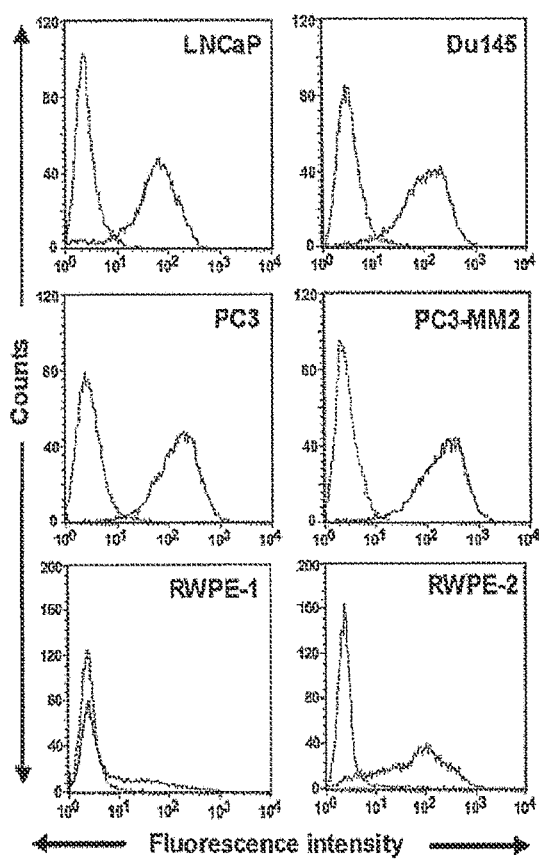
FIG. 1 depicts the binding of monoclonal antibody F77 to various prostate cancer cells using flow cytometry analysis: androgen-dependent prostate cancer cells of the LNCaP cell line; androgen-independent prostate cancer cells of the Du145 and PC3 cell line; highly metastatic prostate cancer cells of the PC3-MM2 cell line, which are derived from PC3 cells; normal human prostate epithelial cells of the RWPE-1 cell line, which are immortalized by HPV-18; and tumorigenic prostate epithelial cells of the RWPE-2 cell line, which were was derived from RWPE-1 cells via Ki-ras oncogene transfection. (MAb F77 staining, bold line; negative control (irrelevant) mouse IgG3 staining, dashed line).

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, double-stranded, or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

"Polypeptide" refers to any peptide or protein comprising amino acids joined by peptide bonds or modified peptide bonds. "Polypeptide" refers to short chains, including peptides, oligopeptides or oligomers, and to longer chains, including proteins. Polypeptides may contain amino acids other than the 20 gene-encoded amino acids. "Polypeptides" include amino acid sequences modified either by natural processes, such as post-translational processing, or by chemical modification or other synthetic techniques well known in the art. Such modifications are well described in the art. Modifications can occur anywhere in a polypeptide, including the peptide backbone, the amino acid side-chains and the amino terminus or the carboxy terminus. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination "Substantially similar" with respect to nucleic acid or amino acid sequences, means at least about 65% identity between two or more sequences. Preferably, the term refers to at least about 70% identity between two or more sequences, more preferably at least about 75% identity, more preferably at least about 80% identity, more preferably at least about 85% identity, more preferably at least about 90% identity, more preferably at least about 91% identity, more preferably at least about 92% identity, more preferably at least about 93% identity, more preferably at least about 94% identity, more preferably at least about 95% identity, more preferably at least about 96% identity, more preferably at least about 97% identity, more preferably at least about 98% identity, and more preferably at least about 99% or greater identity. Such identity can be determined using algorithms known in the art, such as the mBLAST algorithm.

"Antibody" refers to all isotypes of immunoglobulins (IgG, IgA, IgE, IgM, IgD, and IgY) including various monomeric and polymeric forms of each isotype, unless otherwise specified.

"Functional fragments" of such antibodies comprise portions of intact antibodies that retain antigen-binding specificity of the parent antibody molecule. For example, functional fragments can comprise at least the CDRs of either the heavy chain or light chain variable region. Functional fragments can also comprise the heavy chain or light chain variable region, or sequences that are substantially similar to the heavy or light chain variable region. Further suitable functional fragments include, without limitation, antibodies with multiple epitope specificity, bispecific antibodies, diabodies, and single-chain molecules, as well as Fab, F(ab')2, Fd, Fabc, and Fv molecules, single chain (Sc) antibodies (also called ScFv), individual antibody light chains, individual antibody heavy chains, chimeric fusions between antibody chains and other molecules, heavy chain monomers or dimers, light chain monomers or dimers, dimers consisting of one heavy and one light chain, and the like. All antibody isotypes can be used to produce functional fragments of the antibodies herein. Functional fragments can be recombinantly or synthetically produced, with natural or unnatural nucleic acid or amino acid molecules.

The antibodies or functional fragments thereof of the disclosed subject matter can be generated from any species. The antibodies or functional fragments thereof described herein can be labeled or otherwise conjugated to various chemical or biomolecule moieties, for example, for therapeutic or diagnostic or detection or treatment applications. The moieties can be cytotoxic, for example, bacterial toxins, viral toxins, radioisotopes, and the like. The moieties can be detectable labels, for example, fluorescent labels, radiolabels, biotin, and the like, which are known in the art.

"Derived from" can mean any method of derivation and does not require possession of an isolated nucleotide or polypeptide molecule. Rather, "derived from" includes the use of algorithms for designing and theoretically testing antigen binding, creating a functionally equivalent antibody or fragment thereof that retains the binding and/or detection specificity of the parent antibody. "Derived from" contemplates the use of antibodies having substantially similar amino acid or nucleotide sequences to a parent antibody, such as F77 MAb.

The antibodies and functional fragments thereof described herein bind "PCLA," Prostate Cancer Lipid-like Antigen, a novel glycolipid-like antigen highly restricted to the prostate cancer cell or prostasome surfaces, as described below in Examples 15 and 16. PCLA is bound by the F77 MAb.

An "anti-PCLA antibody" described herein detects a glycolipid-like antigen as described below in Examples 15 and 16. An "anti-PCLA antibody" includes the F77 MAb, an antibody comprising a light chain variable region as set forth in SEQ ID NO:1 and a heavy chain variable region as set forth in SEQ ID NO:4. An "anti-PCLA antibody" includes an antibody comprising a light chain variable region as set forth in SEQ ID NO:1 or a heavy chain variable region as set forth in SEQ ID NO:4. An "anti-PCLA antibody" may compete for binding with an antibody comprising a light chain variable region as set forth in SEQ ID NO:1 or a heavy chain variable region as set forth in SEQ ID NO:4. An "anti-PCLA antibody" includes an antibody that competes for binding with an antibody comprising a light chain variable region as set forth in SEQ ID NO:1 and a heavy chain variable region as set forth in SEQ ID NO:4. An "anti-PCLA antibody" includes an antibody that competes for binding with an antibody comprising a light chain variable region as set forth in SEQ ID NO:1, or the CDRs identified therein, or a heavy chain variable region as set forth in SEQ ID NO:4, or the CDRs identified theren. An "anti-PCLA antibody" includes an antibody comprising a light chain variable region as set forth in SEQ ID NO: 2 or 3, or the CDRs identified therein. An "anti-PCLA antibody" includes an antibody comprising a heavy chain variable region as set forth in SEQ ID NOs: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43, or the CDRs identified therein. An "anti-PCLA antibody" includes an antibody comprising a light chain variable region as set forth in SEQ ID NO: 2 or 3, or the CDRs identified therein, and a heavy chain variable region as set forth in SEQ ID NOs: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43, or the CDRs identified therein.

The antibodies or functional fragments thereof described herein have binding affinities (in M) for PCLA that include a dissociation constant (KD) of less than $1 \times 10^{-2}$. In some embodiments, the KD is less than $1 \times 10^{-3}$. In other embodiments, the KD is less than $1 \times 10^{-4}$. In some embodiments, the KD is less than $1 \times 10^{-5}$. In still other embodiments, the KD is less than $1 \times 10{-6}$, $2 \times 10^{-6}$, $3 \times 10^{-6}$, $4 \times 10^{-6}$, $5 \times 10^{-6}$, $6 \times 10^{-6}$, $7 \times 10^{-6}$, $8 \times 10^{-6}$, or $9 \times 10^{-6}$. In other embodiments, the KD is less than $1 \times 10^{-7}$, $2 \times 10^{-7}$, or $3 \times 10^{-7}$, $2 \times 10^{-7}$, $3 \times 10^{-7}$, $4 \times 10^{-7}$, $5 \times 10^{-7}$, $6 \times 10^{-7}$, $7 \times 10^{-7}$, $8 \times 10^{-7}$, or $9 \times 10^{-7}$. In other embodiments, the KD is less than $1 \times 10^{-8}$, $2 \times 10^{-8}$, $3 \times 10^{-8}$, $4 \times 10^{-8}$, $5 \times 10^{-8}$, $6 \times 10^{-8}$, $7 \times 10^{-8}$, $8 \times 10^{-8}$, or $9 \times 10^{-8}$. In other embodiments, the KD is less than $1 \times 10^{-9}$, $2 \times 10^{-9}$, $3 \times 10^{-9}$, $4 \times 10^{-9}$, $5 \times 10^{-9}$, $6 \times 10^{-9}$, $7 \times 10^{-9}$, $8 \times 10^{-9}$, or $9 \times 10^{-9}$. In other embodiments, the KD is less than $1 \times 10^{-10}$, $2 \times 10^{-10}$, $3 \times 10^{-10}$, $2 \times 10^{-10}$, $3 \times 10^{-10}$, $4 \times 10^{-10}$, $5 \times 10^{-10}$, $6 \times 10^{-10}$, $7 \times 10^{-10}$, $8 \times 10^{-10}$, or $9 \times 10^{-10}$. In still other embodiments, the KD is less than $1 \times 10^{-11}$, $2 \times 10^{-11}$, $3 \times 10^{-11}$, $4 \times 10^{-11}$, $5 \times 10^{-11}$, $6 \times 10^{-11}$, $7 \times 10^{-11}$, $8 \times 10^{-11}$, $9 \times 10^{-11}$, $1 \times 10^{-12}$, $1 \times 10^{-13}$, $1 \times 10^{-14}$, or $1 \times 10^{-15}$.

The anti-PCLA antibody antibodies described herein are useful for determining the "degree of differentiation" of prostate cancer in a sample or subject. The phrase "degree of differentiation" refers to the stage of progression of cancer, including tumor grade. One skilled in the art understands that as cancers and/or tumors progress, the cancer cells become less differentiated. One skilled in the art understands that some less differentiated cells can become anchorage independent and/or metastatic. One skilled in the art understands that as prostate cancer progresses, the prostate cancer cells may become androgen independent, and such cells may grow or multiply in the absence of androgen. The degree of differentiation may be quantitatively or qualitatively determined. For example, the degree of differentiation of a prostate tumor may be highly differentiated or completely undifferentiated. As a further example, the degree of differentiation may be zero, low, or high.

Whether an antibody or functional fragment thereof "competes for binding" with an antibody from which it is derived can be tested in any number of competitive or comparative assays, some of which are exemplified below. These assays include sandwich ELISA, immunoprecipitation, immunohistochemistry, in vivo imaging, flow cytometry, FACS analysis, and other assays known in the art. Competing for binding can be determined by separate assays in which the antibodies exhibit similar detection or binding characteristics, and need not be used in the same assay to be deemed to compete for binding. Traditional competitive assays in which the antibodies are used in the same assay are also contemplated for a determination of whether an antibody competes for binding with another.

The terms "treating" or "treatment" refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters; including the results of a physical examination, neurological examination, and/or psychiatric evaluations.

"Effective amount" and "therapeutically effective amount" are used interchangeably herein, and refer to an amount of an antibody or functional fragment thereof, as described herein, effective to achieve a particular biological or therapeutic result such as, but not limited to, the biological or therapeutic results disclosed herein. A therapeutically effective amount of the antibody or antigen-binding fragment thereof may vary according to factors such as the disease state, age, sex, and weight of the individual, and the ability of the antibody or functional fragment thereof to elicit a desired response in the individual. Such results may include, but are not limited to, the treatment of cancer, as determined by any means suitable in the art.

It is to be understood that the embodiments described herein are not limited to particular methods, reagents, compounds, compositions or biological systems, which can, of course, vary. It is also to be understood that the terminology used herein is for the purpose of describing the antibodies and functional fragments thereof, and methods of detecting and/or diagnosing and/or treating, and is not intended to be limiting.

Example 1

Statistical Analysis

All of the experiments were repeated at least three times unless otherwise indicated. The data were expressed as mean±SD. Statistical analysis was performed using Student's t test. The criterion for statistical significance used was $P<0.05$.

Example 2

Cell Lines

PC3, Du145, LNCaP, RWPE-1, and RWPE-2 cells were obtained from the American Type Culture Collection (Manassas, Va.). PC3-MM2 cells were purchased from Dr. Isaiah J. Fidler at U.T.M.D. Anderson Cancer Center.

The RWPE-1 cell line of non-tumorigenic human prostatic epithelial cells was developed by immortalization of epithelial cells that were derived from the peripheral zone of a normal human prostate. The RWPE-2 human prostatic carcinoma cell line was derived from RWPE-1 by transformation with Ki-ras.

RWPE-1 and RWPE-2 Cells were maintained per the manufacturer's instructions in Keratinocyte Serum Free Medium supplemented with bovine pituitary extract and human recombinant epidermal growth factor (K-SFM) (Invitrogen (GIBCO); Kit Catalog Number 17005-042. Other cells lines were maintained in RPMI medium (Invitrogen, Carlsbad, Calif.) containing 5% fetal bovine serum (Hyclone, Logan, Utah).

Example 3

Immunohistochemistry Staining

All the cases were retrieved from the surgical pathology files at the University of Pennsylvania Medical Center. Immunohistochemical staining with the F77 MAb was performed on 5 μm paraffin embedded tissues including TMA (tissue microarray) sections. Briefly, sections were deparaffinized in xylene and rehydrated in graded alcohols. A heat-based antigen retrieval method was used in citrate buffer (pH 6.0) in a microwave oven. F77 MAb (5 μg/ml diluted in Dako© Antibody Diluent) was added and incubated for 30 minutes at room temperature. Slides were washed 5 times with Tris-buffered saline containing Tween 20© reagent (TBST, pH 7.6; DAKO©, Carpinteria, Calif.) and incubated for 30 minutes at room temperature with horseradish peroxidase-labeled dextran polymer coupled to anti-mouse (DAKO© EnVision© System HRP, DAKO). Slides were then washed 3 times with TBST, developed with diaminobenzidine, and counterstained with hematoxylin. The negative control lacked the primary antibody. Immunohistochemical staining of F77 MAb was interpreted semi-quantitatively by assessing the intensity of staining on the entire tissue sections or TMA cores by two board certified pathologists.

Example 4

Flow Cytometry Assay

Cells ($0.5-1\times10^6$) were resuspended in 100 μl FACS buffer (1% BSA/PBS) containing 1 μg F77 MAb and incubated on ice for 20 minutes. After being washed twice with FACS buffer, cells were incubated with FITC labeled goat anti-mouse antibody (1:100; Jackson ImmunoResearch) for 30 minutes on ice before analysis on a BD FACSCalibur using CellQuest Pro software. Cell sorting was carried out on FACSVantage SE with FACSDiVa Option-DiVa software in

Example 5

MTT Assay

Prostate cell lines PC3 and Du145 were aliquoted (1000 cells/well) into 96-well flat-bottom plates. The next day, the cells were treated with 1, 5, and 25 µg/ml F77 MAb or a murine IgG3 (negative control) in the presence of 1% or 10% mouse serum or human serum. Cells were incubated for 3 days at 37° C. before the addition of 3-(4,5-Dimethyl-2-thiazolyl)-2,5-diphenyl-2H-tetrazolium bromide (MTT) to each well, and absorbance was determined at 570 nm.

Example 6

ADCC Assay

Cytotoxic activity was assessed by using the CytoTox 96® Non-Radioactive Cytotoxicity Assay (Promega). Effector U937 cells were treated with IFN-γ (100 unit/mL) for 12-24 hours and then washed 3 times with serum-free medium and incubated for 2 hours to allow detachment of IgG possibly absorbed from bovine serum, as described in Akiyama Y, et al., 1984, Cancer Res., 44, 5127-5131, incorporated by reference herein. Prostate cancer cell lines PC3 and Du145 were target cells, while A431 was the control cell line. For ADCC assays, F77 MAb was incubated with target cells ($10^4$/well) for 20 minutes before addition of effector cells. After 8-16 hour incubation at 37° C., 50 µl supernatant was removed from each well, transferred to an enzymatic assay plate, mixed with 50 µl reconstituted substrate mix, and incubated for 30 minutes at room temperature (protected from light). Stop solution (50 µl) was added to each well and absorbance at 490 nm recorded. Each test was performed in triplicate. The results are expressed as the percentage of lysis (ADCC %).

Example 7

Monoclonal Antibody F77 MAb Specifically Recognizes Prostate Cancer Cells and Tissues Flow cytometry analysis, performed as described in Example 3, of the murine IgG3 F77 MAb binding reveals that its targeting antigen is expressed at a high levels on androgen-independent prostate cancer cell surfaces (PC3-MM2, PC3, and Du145) and at a slightly lower level on the androgen-dependent LNCaP cell surfaces (FIG. 1). F77 MAb shows very limited binding to certain cell lines of mammary or ovarian origin but fails to bind to any cell lines from lung, kidney or skin (FIG. 2). SW260 colon cancer cells and BxPC3 pancreatic cancer cells exhibit weak staining by F77 MAb.

Figures 3A, 3B, 3C, 3D:
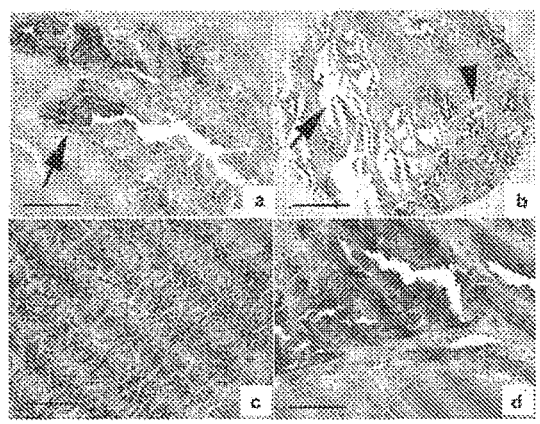
FIG. 3A is a photographic image depicting immunohistochemical staining of benign prostate glands tissue with monoclonal antibody F77, demonstrating a mosaic staining pattern of some benign prostate glands. (Arrow indicates F77-positive prostate gland; scale bar=100 μm).
FIG. 3B is a photographic image depicting immunohistochemical staining of benign and cancerous prostate gland tissue showing the typical result that benign prostate gland tissue is not bound by MAb F77 (arrow), whereas cancerous prostate gland tissue is bound (arrow). (scale bar=200 μm).
FIG. 3C is a photographic image depicting immunohistochemical staining of high grade prostate cancer tissue, demonstrating that poorly differentiated prostate cancer tissues exhibit diffuse staining with MAb F77. (scale bar=50 μm).
FIG. 3D is a photographic image depicting immunohistochemical staining of bone metastatic prostate cancer tissue, demonstrating that cancerous glandular tissue in a bone metastasis also stain diffusely positive with MAb F77. (scale bar=25 μm).
Figure 3E:
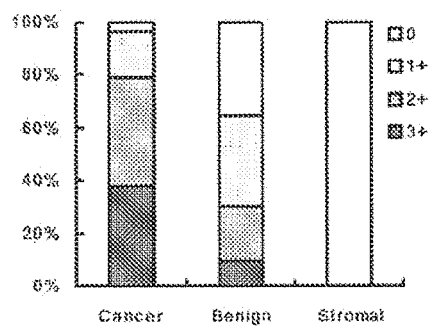
FIG. 3E is a bar graph showing quantification of the immunohistochemical staining in 116 specimens stained with MAb F77 (1 μg/ml) (staining intensity grading: 0 (negative), 1+(weak), 2+(moderate) and 3+(strong)).

F77 MAb immunohistochemistry was performed, as described in Example 2, on a wide range of prostate normal and cancerous tissues. F77 MAb staining was significantly more intense in prostate cancerous tissues than in benign tissues, whereas F77 MAb only showed focal staining on a subpopulation of prostate glandular cells (FIG. 3A). Using primary prostate cancer tissue microarrays, we found that 112 of 116 (96.6%) prostate tissue cores were positive for F77 MAb staining (FIG. 3B). The 4 negative cases were well-differentiated prostate carcinomas. Some minimal staining was observed in a small fraction of small blood vessels in human brain. In addition, 29 of 34 (85.3%) of metastatic prostate cancers stained positively with F77 MAb. No specific staining was found in normal or tumor tissues of human colon, kidney, cervix, pancreas, lung, skin and bladder (FIG. 2). These results indicate that the antigen of the F77 MAb is highly restricted to prostate and over-expressed in prostate tumors.

Example 8

The F77 MAb Positive Subpopulation of RWPE-1 Cells Displays Tumorigenic Phenotype F77 MAb binds to a small population (<10%) of the non-tumorigenic human prostate epithelial cell line RWPE-1, but binds with greater intensity to >80% of tumorigenic RWPE-2 cells that were derived from RWPE-1 after transfection with the constitutively active Ki-ras oncogene (FIG. 1). RWPE-2 cells that express the antigen recognized by the F77 MAb grow faster and display enhanced colony-forming activity when compared to RWPE-1 cells which are not recognized by F77 MAb. Most importantly, the parent RWPE-1 cells do not form tumors when injected into nude mice, whereas RWPE-2 cells do. These data show that the F77 MAb and or an antibody that would compete for binding with F77 MAb, detects a cell surface biomarker indicative of malignant transformation of prostate cells such as RWPE-1.

Figure 4A:
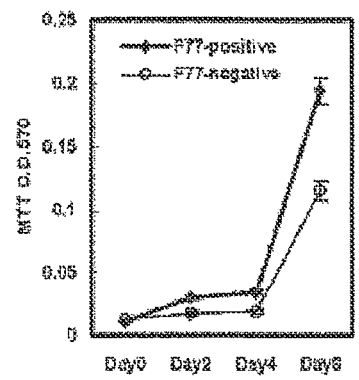
FIG. 4A depicts a graph plotting cell number, as measured by absorbance readings in a colorimetric MTT assay, at specific time points, of two subpopulations of RWPE-1 cells sorted by flow cytometry: one that bound F77 MAb antibody (F77+/RWPE-1) and the other that did not (F77−/RWPE-1). The graph demonstrates that the RWPE-1 subpopulation of cells that express the F77 antigen, to which the F77 MAb binds, grow twice as fast as the RWPE-1 cells that donot express the F77 antigen.
Figure 4B:
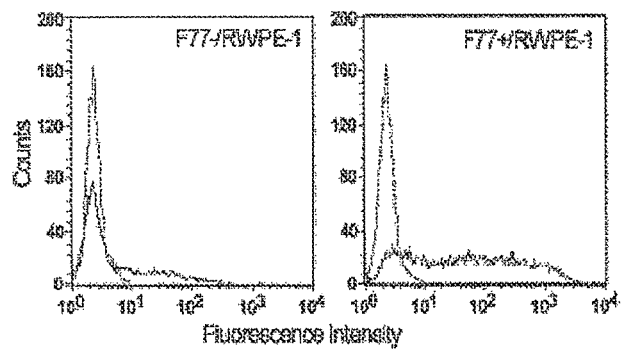
FIG. 4B shows the results of flow cytometry analysis of the F77-positive and F77-negative RWPE-1 subpopulations after 7 days of in vitro cell culture and quantification of staining with F77 MAb, demonstrating that the subpopulation of RWPE-1 prostate cancer cells that bind F77 MAb (F77$^+$/RWPE-1) maintained a high level of expression of the F77 antigen on their surfaces, and exhibit comparable levels of staining to that exhibited by RWPE-2.

To address whether expression of the antigen recognized by F77 MAb is associated with the tumorigenic phenotype of prostate epithelial cells, RWPE-1 cells were stained with F77 MAb and sorted into positive and negative subpopulations by FACS. After 7 days of in vitro cell culture, the subpopulation of RWPE-1 cells that bind F77 MAb (F77$^+$/RWPE-1) maintained a high level of expression of the antigen on their surfaces with a comparable staining level to that exhibited by RWPE-2. The growth of this subpopulation of RWPE-1 cells that bind F77 MAb was twice as fast as that of the subpopulation of RWPE-1 cells that do not bind F77 MAb (F77$^-$/RWPE-1) (FIG. 4).

Next, the ability of the negatively and positively staining subpopulations of RWPE-1 cells to initiate tumors in nude mice was examined (FIG. 5). Immediately after cell sorting, cells were mixed at a 1:1 dilution with Matrigel (BD bioscience) and injected into nude mice ($0.5 \times 10^6$ cells/mouse). As a positive control for tumor formation, tumorigenic RWPE-2 cells were also injected. Significantly, injection of F77$^+$/RWPE-1 cells resulted in tumors in 4/6 of mice, the same tumor formation ratio resulting from injection of tumorigenic RWPE-2 cells (4/6) In contrast, F77–/RWPE-1 cells resulted in a single tumor (1/6). These results demonstrate that RWPE-1 cells that express the antigen recognized by the F77 MAb display increased tumorigenic properties, when compared to prostate epithelial cells that do not express this antigen.

Example 9

Cell Apoptosis Assay (Annexin V/Propidium Iodide)

To assay for apoptosis, tumor cells were first detached by trypsin/EDTA and then washed twice with RPMI medium. Cells were exposed to 3 or 30 µg/ml F77 MAb or appropriate controls in RPMI medium for 2-6 hours at 37° C. in a humidified incubator, 5% CO2. The cells (1×10) were then washed with cold PBS, stained for 15 minutes at room temperature in the dark with 5 µl Alexa Fluor© 488-Annexin V and 1 µl propidium iodide (Vybrant® Apoptosis Assay Kit #2, Invitrogen, V13241), and analyzed by dual color flow cytometry.

Example 10

The F77 Monoclonal Antibody Induces Apoptosis in Prostate Cancer Cells

PC3 cells exposed to F77 MAb for 4 hours were prepared counterstained with Annexin V and propidium iodide as described in Example 5 (FIG. 6A). Cells stained with Annexin V alone represent cells at an early-stage of apoptosis, whereas cells stained with both Annexin V and propidium iodide represent cells at a more advanced stage of apoptosis/necrosis. PC3 cells exposed to 3 µg/ml F77 MAb displayed 4% staining with Annexin V alone and 8% staining with Annexin V and propidium iodide, indicating that the interaction of F77 MAb with its cognate antigen on cells predisposes the cells to modest levels of apoptosis. Less than 1% of PC3 cells exposed to control murine IgG3 displayed staining with Annexin V alone, and there was no difference between F77 MAb and control IgG3 on control cell line A431.

Example 11

Monoclonal Antibody F77 Induces Complement Dependent and Antibody Dependent Cytotoxicity in Prostate Cancer Cells In Vitro and In Vivo It has been reported that Mouse IgG3 antibodies can mediate both complement dependent cytotoxicity (CDC) and antibody dependent cellular cytotoxicity (ADCC), as described in Carter P J, 2006, Nat Rev Immunol, 6, 343-357, which is hereby incorporated by reference herein. F77 MAb-induced CDC was evaluated using cell viability as measured by MTT assays performed according to Example 5. FIG. 6B shows that the presence of 1% of either mouse or human serum as a source of complement remarkably decreased the number of viable cells. A 32% reduction of viable Du145 cells and 43% reduction of PC3 cells was observed in cells with 25 µg/ml F77 MAb in 1% mouse serum. Cells treated with F77 MAb in the absence of complement, i.e. cells grown in serum-free medium or in heat-inactivated serum, only show a limited decrease in cell viability (about 4%) in a standard MTT assay. Percent growth inhibition [(control wells-treated wells)/control wells×100] increased in response to the addition of either mouse or human serum, indicating F77 MAb induced CDC.

Antibody-dependent cell-mediated cytotoxicity (ADCC) of F77 MAb against prostate tumor cells was examined in vitro by lactate dehydrogenase (LDH)-release assay. IFN-$\gamma$ stimulated U937 cells, which are monocyte-like cells, were used as effector cells, as described in Akiyama Y, et al., 1984, Cancer Res., 44, 5127-5131, which is incorporated by reference herein. FIG. 6C presents a significant increase on cytolysis by 10 µg/ml F77 MAb at an effector: target cell ratio of 2:1, revealing 28% cytotoxicity of Du145 and 18% of PC3 cells. The ADCC effect was antigen-specific, since A431 cells which lack the F77 antigen were not affected.

Example 12

Xenograft Mouse Models for Measuring Prostate Tumors In Vivo

Tumor xenografts were generated by s.c. injection of 0.5× $10^6$ A431 or 1-2×$10^6$ PC3 or Du145 cells with or without Matrigel© (BD bioscience) in the flanks of male NCr athymic-nu/nu mice (Charles River Laboratory, Wilmington, Mass.). Antibody i.p. injection started at day 7 or 11 after tumor cell implantation. Control mice were injected with irrelevant mouse IgG or PBS, which had no effect on tumor growth. Tumor size was determined by vernier caliper measurements, and the tumor volume was calculated as length× width×height ($mm^3$).

Example 13

F77 MAb Inhibits Growth of Prostate Tumors In Vivo

To determine if the effects of F77 MAb could inhibit androgen-independent prostate tumor growth in vivo, the antibody was given to mice transplanted with PC3 or Du145 tumor cells. In the first series of experiments, nude mice were injected with PC3 cells, to which F77 MAb binds, on the right flank and A431 cells, to which MAb does not bind, on the left flank. For each injection, PC3 ($10^6$ cells/mouse) and A431 cells (0.5×$10^6$ cells/mouse) were administered. Antibody injection (i.p.) started when tumors were first palpable, i.e. had reached a size of 2-4 $mm^3$, at day 7 after injection of tumor cells. F77 MAb was administrated 4 times (200 µg/dose at days 7 and 9, and 100 µg/dose at days 11 and 13). A mouse IgG negative control (200 µg/dose) or vehicle (PBS) was also used.

PBS was used as the vehicle control. Mice were sacrificed when tumors were greater than 1 cm in diameter in accordance with the University of Pennsylvania's IACUC. 1×$10^6$ Du145 (MAb F77 or a control mouse IgG was administered at Day 7 by i.p. injection of 200 µg/dose every other day for 4 times totally(C). Post-treatment (D) started at Day 11 when tumor volume was greater than 30 mm3. (mean tumor volume (mm3)±SEM. P≤0.01)

Figures 7A, 7B, 7C, 7D:
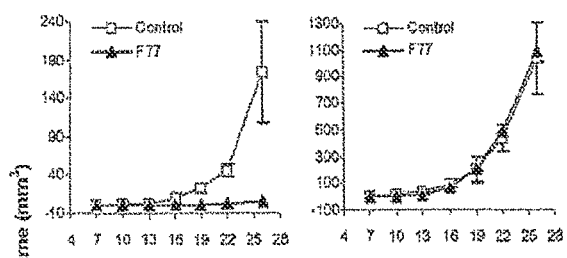
FIG. 7A is a graph demonstrating that F77 MAb inhibits growth of prostate tumors in vivo. The graph plots tumor volume versus time for response to treatment with F77 MAb or control (PBS) in male nude mice 7 days following subcutaneous (s.c.) injection with 1×10$^6$ PC3 cells in the right flank. Treatment of MAb F77 or control corresponds to i.p. injection of 200 μg/dose at Day 7 and 9, 100 μg/dose at Day 11 and 13.
FIG. 7B is a graph demonstrating that F77 MAb does not inhibit growth of tumors of A431 cells (human epithelial carcinoma cell line which do not bind F77 MAb). The graph plots tumor volume versus time for response to treatment with F77 MAb or control (PBS) in male nude mice 7 days after subcutaneous (s.c.) injection with 0.5×10$^6$ A431 cells in the left flank. Treatment of MAb F77 or control corresponds to i.p. injection of 200 μg/dose at Day 7 and 9, 100 μg/dose at Day 11 and 13. (mean tumor volume (mm$^3$)±SEM. P≤0.01).
FIG. 7C is a graph demonstrating that F77 MAb prevents growth of Du145 prostate tumors in vivo. The graph plots tumor volume versus time for response to treatment with F77 MAb or control (PBS) in male nude mice 7 days following subcutaneous (s.c.) injection with 2×10$^6$Du145 cells. Treatment of MAb F77 or control corresponds to i.p. injection of 200 μg/dose at Day 7 and 9, 100 μg/dose at Day 11 and 13. (mean tumor volume (mm$^3$)±SEM. P≤0.01)
FIG. 7D is a graph demonstrating that F77 MAb inhibits growth of larger, established Du145 prostate tumors in vivo. The graph plots tumor volume versus time for response to treatment with F77 MAb or control (PBS) in male nude mice with tumors with a mean size of 135 mm$^3$, at 11 days following subcutaneous (s.c.) injection with 2×10$^6$ Du145 cells. Treatment of MAb F77 or control corresponds to i.p. injection of 200 μg/dose at Day 7 and 9, 100 μg/dose at Day 11 and 13. (mean tumor volume (mm$^3$)±SEM P≤0.01).
Figure 8:
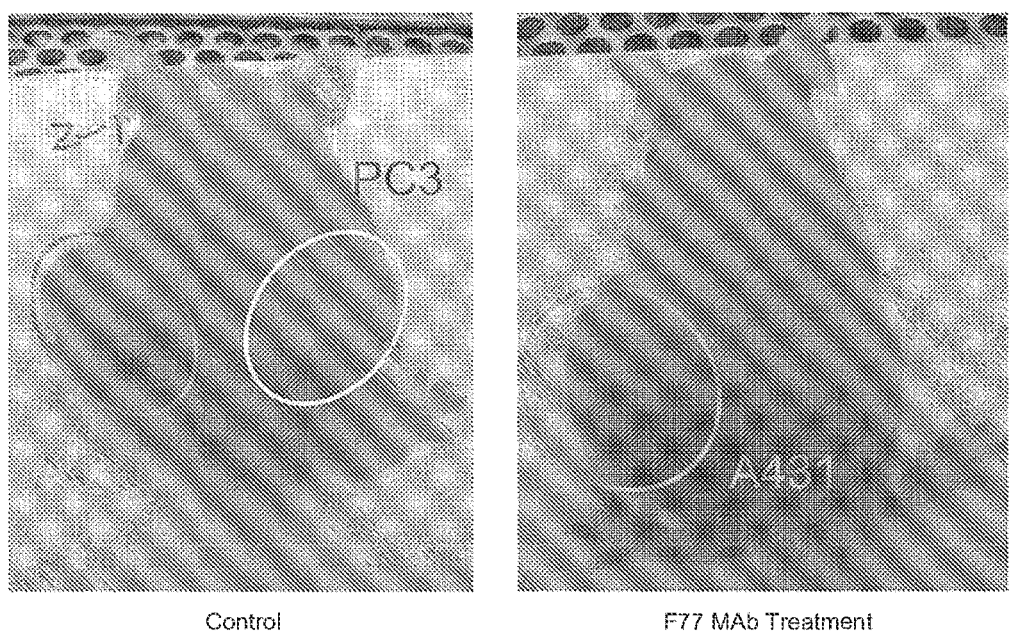
FIG. 8 is a photographic image of mice depicting typical results of the experiment of FIG. 7A, demonstrating that F77 MAb treatment shrinks PC3 tumors but not A431 tumors.

Treatment with F77 MAb inhibited PC3 tumor growth. In fact, PC3 tumor growth was completely suppressed in 5 out of 6 mice in the F77 MAb treatment group. In the one mouse that developed a tumor, only a small tumor was palpated (volume=6 $mm^3$). Mice (n=6) in the vehicle control group all developed tumors with an average volume of 182.5 $mm^3$ at Day 28 (FIG. 7A). A431 tumors were not affected by F77 MAb treatment and grew aggressively with a mean size of 1200 $mm^3$ by day 28 when they had to be sacrificed (FIG. 7B). A photograph of typical results of F77 MAb treatment on PC3 and A431 tumors in vivo in mice is shown in FIG. 8.

Inhibition of tumor formation was also observed on Du145 tumors treated with F77 MAb. The Du145 group-I was treated following the same protocol as the PC3 group above. Administration of F77 MAb to Du145-injected mice resulted in complete inhibition of tumor growth until day 30 as compared with control mice treated with mouse IgG control (FIG. 7C).

In Du145 group-II, the effectiveness of F77 MAb on larger established tumors was studied. 2×$10^6$ D145 cells were injected in each mouse in this group (n=6). F77 MAb (200 µg/dose) was administrated every other day for a total of 4 injections, starting at Day 11 when the mean size of the Du145 tumor was about 35 $mm^3$. A significant reduction (P<0.01) in tumor-growth rate was detected in F77 MAb treated mice as compared with control mice (FIG. 7D). At day 28, 10 days after the last antibody injection, tumors in the F77 MAb-treated mice reached a mean volume of 71.7 $mm^3$, whereas the control mice developed tumors with mean volume of 180.4 $mm^3$. Thus, these results demonstrate that F77 MAb is able to inhibit androgen-independent prostate tumor formation in both the PC3 and Du145 established tumor models.

Example 14

Isolation of Lipid Rafts and Extraction of the Antigen Bound by F77 MAb by Chloroform/Methanol For the chloroform/methanol extraction, a $2\times10^8$ cell pellet was homogenized with 3 volumes of distilled water. The homogenate was poured into 10.8 volumes of methanol at room temperature and then 5.4 volumes of chloroform were added. The mixture was stirred for 30 minutes and was then filtered. 3.5 volumes of water were added. The solvents were carefully mixed by turning the glass tube up and down several times. When the 2 phases were distinctly separated, the upper phase was collected and evaporated to dryness. The residue was resuspended in water or methanol for the subsequent analysis. Such extractions are described in Svennerholm L, et al., 1980, Biochim Biophys Acta, 617, 97-109, which is hereby incorporated by reference.

Lipid raft microdomains on the cell membrane are resistant to mild detergent such as Triton X100 or CHAPS at 4° C., but are soluble in RIPA buffer. Thus, to whether F77 MAb binds lipid rafts, the lipid rafts were isolated. To do so, cells (PC3, Du145, LNCaP, and negative control A431) were treated with 0.5% CHAPS buffer (25 mM Tris pH 7.5, 5 mM EDTA, 150 mM NaCl, containing 0.5% CHAPS) on ice for 30 minutes, and then lipid rafts were isolated by ultracentrifugation at 100,000×g for 1 hour at 4° C. The CHAPS-insoluble pellets containing the rafts were solubilized in RIPA buffer (25 mM Tris pH 7.5, 5 mM EDTA, 150 mM NaCl, containing 0.1% SDS, 1% Triton X100™ detergent, and 0.5% sodium deoxycholate).

Example 15

F77 MAb Binds Lipid Raft Fractions

The antigen bound by F77 MAb could not be resolved by conventional protein SDS-PAGE. The F77 MAb antibody did not detect any protein bands in Western-blotting. (Data not shown).

Figure 9A:
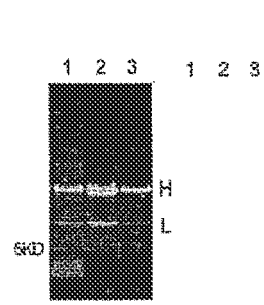
FIG. 9A depicts two images of an electrophoretic gel resolving immunoprecipitates of PC3 and A431 cells lysed in RIPA buffer ($10^7$ cells/1 mL RIPA buffer) using F77 MAb or control IgG. The left image shows initial staining of the electrophoretic gel with Pro-Q Emerald 300 carbohydrate fluorescent stain visualized with a transilluminator and the right image shows the subsequent staining of the same gel with the Coomassie blue protein stain (Lane 1: lysates of PC3 cells bound and precipitated with 10 µg of monoclonal F77 antibody; Lane 2: lysates of A431 cells bound and precipitated with 10 µg of monoclonal F77 antibody; Lane 3: lysates of control PC3 cells bound and precipitated with 5 µg murine IgG).

Thus, detergent characterization was performed. After immunoprecipitation with F77 MAb, samples were separated by SDS-PAGE (4-16%). A significant band that migrated faster than the dye front (approximately <5KD) was detected in the PC3 sample by carbohydrate staining (Pro-Q© Emerald 300 Gel Stain Kit, Invitrogen), but was not stained by Coomassie blue (FIG. 9A). Pro-Q© Emerald 300 staining is based on the principle of periodic acid/Schiff staining as a way to detect carbohydrate chains in glycoproteins or glycolipids, as described in Tatituri R V, et al., 2007, J Biol Chem, 282, 4561-4572, which is incorporated by reference herein.

To further identify the nature of the antigen recognized by F77 MAb, PPMP (1-phenyl-2-palmitoylamino-3-morpholino-1-propanol), a potent inhibitor of glycosphingolipid synthesis, was added to cell cultures at a concentration of 5 μg/ml or 20 μg/ml for 72 hours. To prevent glycosylation of glycoproteins, the cells were cultured for 48-72 hours with 2-4 mM 0-glycosylation inhibitor benzyl-N-acetyl-alpha-galactosaminide (Benzyl-α-GalNAc; Sigma B4894) or 0.5-2 μg/mL N-glycosylation inhibitor Tunicamycin (Sigma), as described in Paul P, et al., 1992, Anal Biochem, 204, 265-272, which is incorporated by reference herein.

Figure 9B:
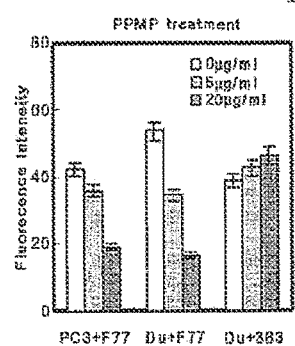
FIG. 9B is a bar graph demonstrating that treatment (48 hours) with the glycosphingolipid inhibitor PPMP induces a dose-dependent decrease in the level of the antigen recognized by the F77 MAb on both PC3 and Du145 (Du) cell surfaces as analyzed by flow cytometry. (3B3=control anti-CD147 monoclonal antibody).

PPMP inhibits the synthesis of most glycosphingolipids by blockade of the enzyme glucosylceramide synthase, as described in Abe A, et al., 1992, J Biochem, 111, 191-196, which is hereby incorporated by reference. Glycosphingolipids are the most common glycolipids in mammals, as described in 21. Hakomori S, 2003, Curr Opin Hematol, 10, 16-24, which is hereby incorporated by reference. PPMP caused a significant dose-dependent decrease of F77 antigen on both PC3 and Du145 cell surfaces but did not have a specific effect on the glycoprotein CD147 (FIG. 9B). While the raw data appear to show an effect, the modest increase of CD 147 levels was due to a decrease in cell viability after PPMP treatment. Two widely used inhibitors of protein glycosylation, Tumicamycin and Benzyl-α-galNAc, had no effect on F77 antigen expression (data not shown).

The data indicate that MAb F77 recognizes a unique prostate-specific glycolipid, termed PCLA (prostate cancer lipid-like antigen).

Figure 9C:
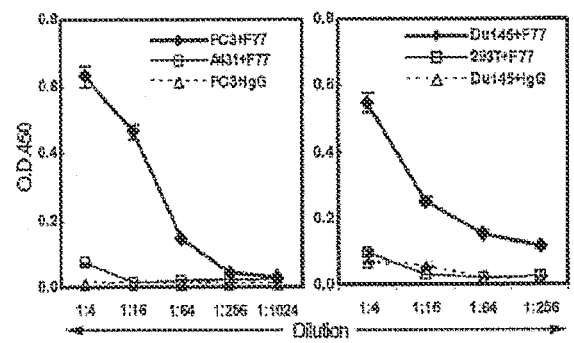
FIG. 9C is two graphs depicting the specific binding of F77 MAb to glycolipids extracted from PC3 and Du145, and the lack of binding of F77 MAb to glycolipids extracted from control cell lines HEK293 and A431, as measured in an ELISA with F77 antibody (1 µg/ml or control anti-CD147 monoclonal antibody 3B3 (murine IgG3).

Moreover, glycolipid levels, as extracted in chloroform/methanol/water (1:2:1.4), of different cell lines were analyzed by lipid ELISA. For the assay, a four-fold dilution of the antigen samples was made in methanol. Immediately before addition to microplate wells, sample dilutions were mixed well with an equal volume of water. A 50 μl aliquot was then pipetted into each well of a 96-well flat bottom plate. The solvent was allowed to evaporate at room temperate for 12 hours. The plates were blocked by 1% BSA/PBS for 2 hours at RT. After 3 washes with PBS, F77 antibody or control mouse antibody was diluted with PBS, and 500 was added to each well. After 90 minutes of incubation, the plates were washed 3 times with PBS. Secondary antibody (1:5000 diluted HRP-goat anti-mouse, GE Healthcare) was then added and the plates were incubated for 1 hour at RT. The plates were washed 5 times; the color was developed with TMB (Sigma) and measured at 450 nm; such procedures are known in the art. F77 MAb displayed specific binding to the glycolipid extracts from PC3 and Du145 in a concentration-dependent manner, but there was no binding to extracts of control human A431 and HEK293 cells (FIG. 9C).

Figure 10A:
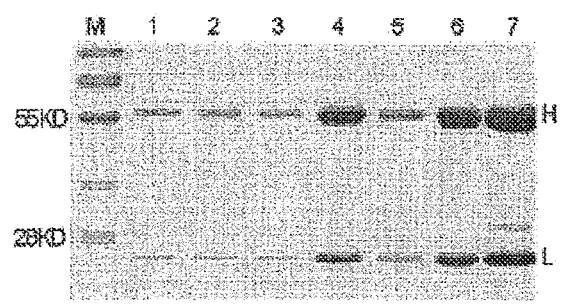
FIG. 10A is an image of an electrophoretic gel resolving F77 MAb immunoprecipitates (50 µg MAb F77 per $5 \times 10^7$ cells for 30 minutes) of lysed Du145, LNCaP, and PC3 prostate cells subject to a lipid raft isolation procedure. (Lane 1: Du145+F77/CHAPS; Lane 2: LNCaP+F77/CHAPS; Lane 3: PC3+F77/CHAPS; Lane 4: Du145+F77/RIPA, Lane 5: LNCaP+F77/RIPA; Lane 6: PC3+F77/RIPA; Lane 7: the total amount of MAb F77 added in each sample; for each Lane: H, heavy chain; L, light chain)
Figure 10B:
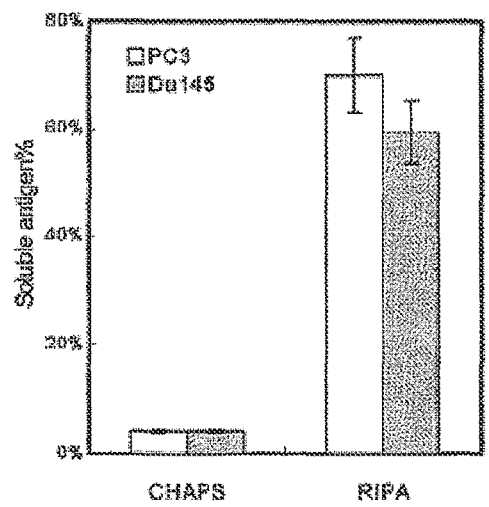
FIG. 10B is a bar graph of the relative levels of F77 antigen soluble in CHAPS buffer and RIPA buffer as measured by the relative intensity of Coomassie blue stained bands on SDS-PAGE. The graph demonstrates that when cells are treated with 0.5% CHAPS on ice, only 4% of PC3 and Du145 cell surface stained with F77 MAb.

Recent studies have revealed that glycolipids in cell membranes are preferentially distributed into lipid microdomains, termed lipid rafts as described in Brown D A, et al, 1998, Annu Rev Cell Dev Biol, 14, 111-136, which is incorporated by reference herein. Thus, the association of the glycolipid-like F77 antigen with lipid rafts on cell surfaces was studied. Lipid rafts can be isolated biochemically as detergent-insoluble fractions of cells are treated with Triton X100 or CHAPS on ice. 0.5% CHAPS lysis buffer was used to treat prostate cancer cells after the surfaces were saturated with F77 MAb (~8 μg/$10^7$ cells). Since F77 MAb was pre-bound to the antigen to form antibody-antigen complexes prior to detergent treatment, protein G beads were used to capture the antibody-antigen complexes from the supernatant. The amount of F77 MAb was used as an indicator of detergent-soluble cognate antigens (FIG. 10).

Using this detection system, only 4% of F77 antigen was soluble in 0.5% CHAPS (FIG. 10), demonstrating that the glycolipid-like F77 antigen is in detergent-insoluble fractions (namely lipid rafts). RIPA buffer treatment can disrupt lipid rafts. Indeed, RIPA buffer releases a large percentage of F77 antigens (70%) from PC3 and (60%) from Du145 cell membranes. Taken together, these studies indicate that the F77 antigen is a glycolipid-like small molecule located in lipid raft microdomains on prostate cancer cell surfaces.

Example 16

Isolation and Immunodetection of Prostasomes

The cells were grown in 150 mm plates. When cells reached 80% confluence, they were washed twice with RPMI medium without FBS and then were maintained in serum-free RPMI medium for 24-48 hours. Cell death, as determined by trypan blue exclusion, was not observed under these conditions. Cell culture medium was collected and centrifuged at 10,000 g for 30 min to remove possible cell debris. The supernatant was subsequently subjected to ultracentrifuga-

Example 17

Immunoreactivity of Y77 MAb to Prostasomes

Figure 11A:
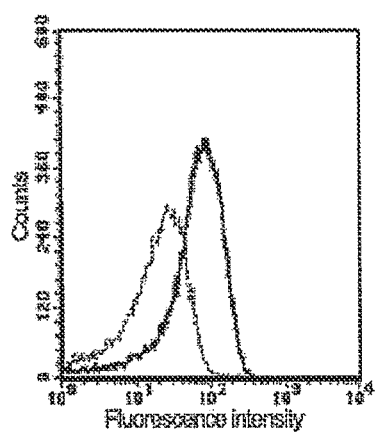
FIG. 11A is an graph of the results of F77 MAb binding to prostasome pellets using flow cytometry analysis using a BD FACSCalibur© instrument; prior to analysis, prostasome samples were incubated with 1 µg/100 µl DyLight-488 labeled MAb F77 (bold line) or mouse IgG3 control (dashed line) for 30 minutes.
Figure 11B:
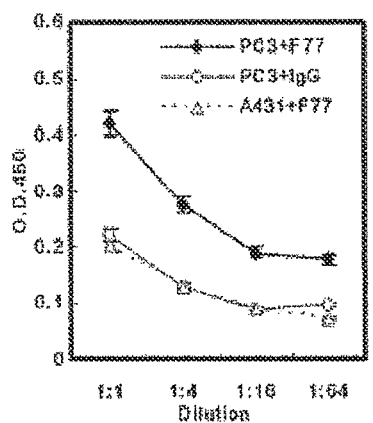
FIG. 11B is a graph plotting the absorbance readings in an ELISA assay of prostasome pellets isolated from one 150 mm cell culture dish of PC3 or A431 cells that were resuspended in 100 µl PBS for subsequent studies. Plates were coated overnight with 5 µg/ml F77 MAb in coating buffer (0.1 M NaHCO3, pH 9.6) and blocked by incubation with 200 µl/well of 1% BSA/PBS, followed by addition of Prostasome samples diluted with PBS (1:1-1:64), 2 hours of incubation at room temperature, and subsequent addition of 1-5 µg/ml biotinylated-F77 MAb or control mouse IgG was added to wells. After washing, streptavidin-HRP (GE healthcare) was then added for 1 hour incubation and absorbance measurements taken.
Figure 12:
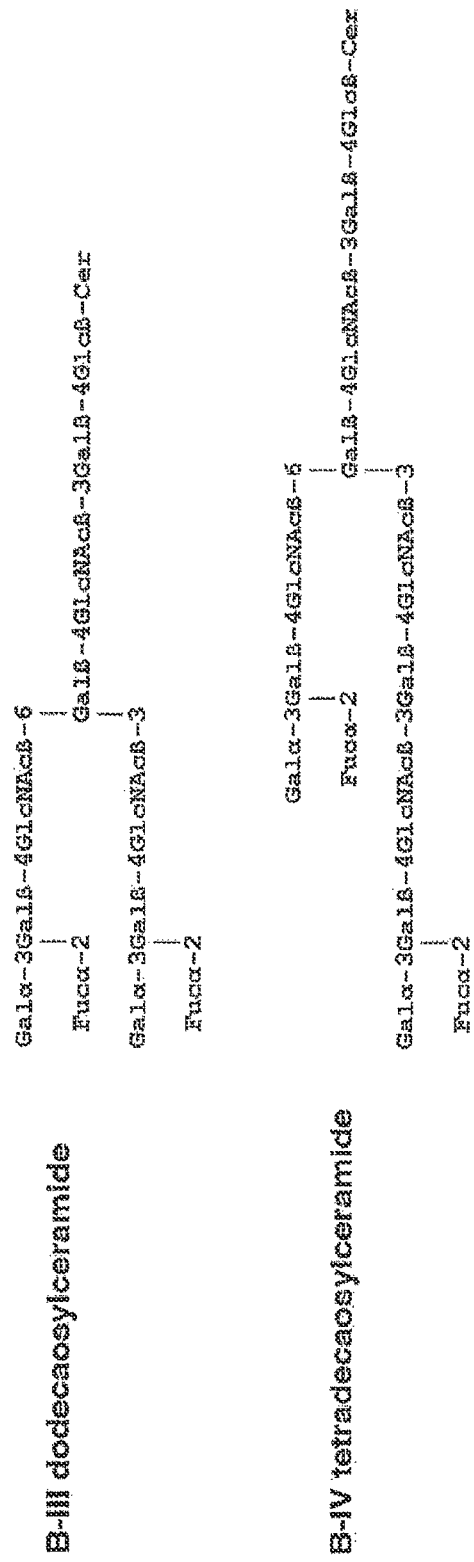
FIG. 12 depicts the two epitopes recognized by F77 MAb in neoglycolipid (NGL)-based microarrays, namely B-III dodecaosylceramide and B-IV tetradecaosylceramide.

PCLA was detected on prostasomes isolated from PC3 medium by a sandwich-ELISA and flow cytometry employing F77 MAb. For both experiments, prostasome pellets were isolated, as described in Example 16, from one 150 mm cell culture dish and resuspended in 100 µl PBS for subsequent studies. For the flow cytometry study, prostasome samples were incubated with 1 µg/100 µl DyLight-488© (Pierce, Rockford, Ill.) labeled F77 MAb (bold line) or mouse IgG3 control (dashed line) for 30 mins and then analyzed using a BD FACSCalibur (FIG. 11A). For the sandwhich ELISA, plates were coated overnight with 5 µg/ml F77 MAb in coating buffer (0.1 M NaHCO3, pH 9.6). Additional binding sites were blocked by incubation with 200 µl/well of 1% BSA/PBS. Prostasome samples diluted with PBS (1:1-1:64) were then added. After 2 hours of incubation at room temperature, 1-5 µg/ml biotinylated-F77 MAb or control mouse IgG was added to wells. The plates were incubated for 1 hour at RT and washed 3 times with PBS. 1:3000 diluted streptavidin-HRP (GE healthcare) was then added for 1 hour incubation (FIG. 11B). Together, these assays demonstrate that the F77 MAb is useful for a non-invasive detection using prostasome containing fluid, including semen or serum.

Example 18

Neoglycolipid (NGL)-Based Microarrays

The NGL technology involves the micro-scale conjugation of oligosaccharides to a lipid tag (Feizi, T., M. S. Stoll, et al. (1994). Methods Enzymol 230: 484-519; Chai, W., M. S. Stoll, et al. (2003). Methods Enzymol 362: 160-95). The resulting NGLs can be readily immobilized on matrices in the clustered state and probed for recognition by carbohydrate-binding proteins. For all intents and purposes NGLs behave like glycolipids. An advantage is that they can be arrayed and analysed side by side with glycosphingolipids. A microarray system based on this principle has been developed (Feizi, T. and W. Chai (2004). Nat Rev Mol Cell Biol 5(7): 582-8; Liu, Y., A. S. Palma, et al. (2009). Biol Chem 390(7): 647-56). The current microarray encompasses~500 NGLs derived from glycoproteins and glycosaminoglycans and diverse other mammalian type oligosaccharides. In addition natural and chemically synthesized predominantly mammalian type glycolipids (~160) are included. The probes are robotically arrayed on nitrocellulose-coated glass slides and we have observed that the clustered display with an element of lateral mobility renders their presentation similar to that on cell surfaces.

F77 MAb gave exclusive binding to the two blood group B-related probes having branched polyLacNAc backbone sequences, namely B-III dodecaosylceramide (position 226 in the array set) and B-IV tetradecaosylceramide (position 227 in the array set). This is consistent with our earlier findings in the initial screening experiments. The fucose in these structures may be important, as the 'B-like' analogues (e.g. B-like decaosylceramide, position 209 in the array set) which have similar branched polyLacNAc backbones and the same lipid moieties were not recognized by F77 MAb.

Each of the references cited herein are incorporated by reference in their entirety.

---

What is claimed:

1. A method of preferentially inducing cell death in primary or metastatic prostate cancer cells that express PCLA over non-cancerous prostate cells in a human, comprising administering an anti-PCLA antibody having a variable light chain sequence as set forth in SEQ ID NO: 1 and a variable heavy chain sequence as set forth in SEQ ID NO: 4, wherein the anti-PCLA antibody is capable of inducing ADCC and/or CDC.

* * * * *